US012115194B2

(12) United States Patent
Itescu et al.

(10) Patent No.: US 12,115,194 B2
(45) Date of Patent: *Oct. 15, 2024

(54) PREVENTION OF PROGRESSIVE HEART FAILURE

(71) Applicant: Mesoblast International Sarl, Meyrin (CH)

(72) Inventors: Silviu Itescu, Melbourne (AU); Lee Golden, New York, NY (US)

(73) Assignee: MESOBLAST INTERNATIONAL SARL, Meyrin (CH)

( * ) Notice: Subject to any disclaimer, the term of this patent is extended or adjusted under 35 U.S.C. 154(b) by 73 days.

This patent is subject to a terminal disclaimer.

(21) Appl. No.: 17/964,905

(22) Filed: Oct. 12, 2022

(65) Prior Publication Data

US 2023/0124294 A1   Apr. 20, 2023

Related U.S. Application Data

(63) Continuation of application No. 15/534,376, filed as application No. PCT/EP2015/081048 on Dec. 22, 2015, now Pat. No. 11,491,188.

(30) Foreign Application Priority Data

Dec. 23, 2014  (AU) ................. 2014905240

(51) Int. Cl.
*A61K 35/28* (2015.01)
*A61K 9/00* (2006.01)
*A61K 35/12* (2015.01)
*C12N 5/0775* (2010.01)

(52) U.S. Cl.
CPC ............ *A61K 35/28* (2013.01); *C12N 5/0662* (2013.01); *A61K 9/0019* (2013.01); *A61K 2035/124* (2013.01); *A61K 2300/00* (2013.01)

(58) Field of Classification Search
None
See application file for complete search history.

(56) References Cited

U.S. PATENT DOCUMENTS

2012/0269784 A1   10/2012   Pittenger et al.
2014/0370069 A1   12/2014   Williams et al.

FOREIGN PATENT DOCUMENTS

KR   20130106381 A  *  9/2013   ............... A61P 9/04

OTHER PUBLICATIONS

Hare, J.M. et al. 2009. A randomized, double-blind, placebo-controlled, dose-escalation study of intravenous adult human mesenchymal stem cells (Prochymal) after acute myocardial infarction. Journal of the American College of Cardiology 54(24): 2277-2286; specif. pp. 2277-2280, 2282, 2283, 2285 (Year: 2009).*
EngMT. Hare, J.M. et al. Bone marrow derived CD271 precursor cells for cardiac repair. Korean Patent Application Publication No. KR 20130106381A; Date of Pub.: Sep. 27, 2013; pp. 1-31, specif. pp.1, 7, 22, 23, 24, 29 (Year: 2013).*
Schachinger, V. et al. 2006. Intracoronary bone marrow-derived progenitor cells in acute myocardial infarction. The New England Journal of Medicine 355(12): 1210-1221, specif. pp. 1210, 1211, 1213 , 1215 1220 (Year: 2006).*
Wong, N.D. et al. 1995. Echocardiographic left ventricular systolic function and vols. in young adults: distribution and factors influencing variability American Heart Journal 129(3): 571-577; specif. p. 571 (Year: 1995).*
Cleveland Clinic. Last reviewed 2022. CK-MB test. Datasheet [online]. Retrieved on Mar. 1, 2024. Downloaded from the internet: <https://my.clevelandclinic.org/health/diagnostics/24519-ck-mb-test> pp. 1-11; specif. p. 7 (Year: 2022).*
Psaltis, P.J. et al. 2010. Enrichment for STRO-1 expression enhances the cardiovascular paracrine activity of human bone marrow-derived mesenchymal cell populations. Journal of Cellular Physiology 223: 530-540; specif. pp. 530, 531, 539 (Year: 2010).*
Armiñán A, Gandía C, García-Verdugo JM, Liedó E, Trigueros C, Ruiz-Saurí A, Miñana, MD, Solves P, Payá R, Montero JA, Sepúlveda P. Mesenchymal stem cells provide better results than hematopoietic precursors for the treatment of myocardial infarction. J Am Coll Cardiol. May 18, 2010;55(20):2244-53. doi: 10.1016/j.jacc.2009.08.092. PMID: 20466205. (Exhibit 1).
Bernard A, Addetia K, Dulgheru R, Caballero L, Sugimoto T, Akhaladze N, Athanassopoulos GD, Barone D, Baroni M, Cardim N, Hagendorff A, Hristova K, Ilardi F, Lopez T, de la Morena G, Popescu BA, Penicka M, Ozyigit T, David Rodrigo Carbonero J, van de Veire N, Stephan Von Bardeleben R, Vinereanu D, Luis Zamorano J, Martinez C, Magne J, Cosyns B, Donal E, Habib G, Badano LP, Lang RM, Lancellotti P. 3D echocardiographic reference ranges for normal left ventricular volumes and strain: results from the EACVI NORRE study. Eur Heart J Cardiovasc Imaging. Apr. 1, 2017;18(4):475-483. doi: 10.1093/ehjci/jew284. PMID: 28329230. (Exhibit 2).
Carvalho JL, Braga VB, Melo MB, Campos AC, Oliveira MS, Gomes DA, Ferreira AJ, Santos RA, Goes AM. Priming mesenchymal stem cells boosts stem cell therapy to treat myocardial infarction. J Cell Mol Med. May 2013;17(5):617-25. doi: 10.1111/jcmm.12036. Epub Mar. 14, 2013. PMID: 23490190; PMCID: PMC3665703. (Exhibit 3).
Chen S, Liu Z, Tian N, Zhang J, Yei F, Duan B, Zhu Z, Lin S, Kwan TW. Intracoronary transplantation of autologous bone marrow mesenchymal stem cells for ischemic cardiomyopathy due to isolated chronic occluded left anterior descending artery. J Invasive Cardiol. Nov. 2006; 18(11):552-6. PMID: 17090821 . . . (Exhibit 4).
Cuende N, Rico L, Herrera C. Concise review: bone marrow mononuclear cells for the treatment of ischemic syndromes: medicinal product or cell transplantation? Stem Cells Transl Med. May 2012;1(5):403-8. doi: 10.5966/sctm.2011-0064. Epub May 3, 2012. PMID: 23197819; PMCID: PMC3659705. (Exhibit 5).

(Continued)

*Primary Examiner* — Adam Weidner
*Assistant Examiner* — Sharon M. Papciak
(74) *Attorney, Agent, or Firm* — John P. White

(57) ABSTRACT

The present disclosure relates to methods for preventing progressive heart failure in subjects with persistent left ventricular (LV) dysfunction. Such methods may also be used for treating or preventing progressive heart failure in subjects with a proximal left anterior descending (LAD) lesion and persistent left ventricular dysfunction.

13 Claims, 9 Drawing Sheets

(56) References Cited

OTHER PUBLICATIONS

Eitel I, Desch S, Fuernau G, Hildebrand L, Gutberlet M, Schuler G, Thiele H. Prognostic significance and determinants of myocardial salvage assessed by cardiovascular magnetic resonance in acute reperfused myocardial infarction. J Am Coll Cardiol. Jun. 1, 2010;55(22):2470-9. doi: 10.1016/j.jacc.2010.01.049. PMID: 20510214. (Exhibit 6).

Elsman P, van 't Hof AW, Hoorntje JC, de Boer MJ, Borm GF, Suryapranata H, Ottervanger JP, Gosselink AT, Dambrink JH, Zijlstra F. Effect of coronary occlusion site on angiographic and clinical outcome in acute myocardial infarction patients treated with early coronary intervention. Am J Cardiol. Apr. 15, 2006;97(8):1137-41. doi: 10.1016/j.amjcard.2005.11.027. Epub Feb. 28, 2006. PMID: 16616014. (Exhibit 7).

Gandia C, Armiñan A, García-Verdugo JM, Lledó E, Ruiz A, Miñana MD, Sanchez-Torrijos J, Payá R, Mirabet V, Carbonell-Uberos F, Llop M, Montero JA, Sepúlveda P. Human dental pulp stem cells improve left ventricular function, induce angiogenesis, and reduce infarct size in rats with acute myocardial infarction. Stem Cells. Mar. 2008;26(3):638-45. doi: 10.1634/stemcells.2007-0484. Epub Dec. 13, 2007. PMID: 18079433. (Exhibit 8).

Hajjar RJ, Zsebo K, Deckelbaum L, Thompson C, Rudy J, Yaroshinsky A, Ly H, Kawase Y, Wagner K, Borow K, Jaski B, London B, Greenberg B, Pauly DF, Patten R, Starling R, Mancini D, Jessup M. Design of a phase 1/2 trial of intracoronary administration of AAV1/SERCA2a in patients with heart failure. J Card Fail. Jun. 2008;14(5):355-67. doi: 10.1016/j.cardfail.2008.02.005. Epub May 27, 2008. PMID: 18514926. (Exhibit 9).

Hare JM, Traverse JH, Henry TD, Dib N, Strumpf RK, Schulman SP, Gerstenblith G, DeMaria AN, Denktas AE, Gammon RS, Hermiller JB Jr, Reisman MA, Schaer GL, Sherman W. A randomized, double-blind, placebo-controlled, dose-escalation study of intravenous adult human mesenchymal stem cells (prochymal) after acute myocardial infarction. J Am Coll Cardiol. Dec. 8, 2009;54(24):2277-86. doi: 10.1016/j.jacc.2009.06.055. PMID: 19958962; PMCID: PMC3580848. (Exhibit 10).

Heldman AW, DiFede DL, Fishman JE, et al. Transendocardial Mesenchymal Stem Cells and Mononuclear Bone Marrow Cells for Ischemic Cardiomyopathy: The TAC-HFT Randomized Trial. JAMA. 2014;311(1):62-73. doi:10.1001/jama.2013.282909(Exhibit 11).

Holland R, Rechel B, Stepien K, Harvey I, Brooksby I. Patients' self-assessed functional status in heart failure by New York Heart Association class: a prognostic predictor of hospitalizations, quality of life and death. J Card Fail. Feb. 2010;16(2):150-6. doi: 10.1016/j.cardfail.2009.08.010. Epub Oct. 22, 2009. PMID: 20142027; PMCID: PMC2817782. (Exhibit 12).

Hu X, Yu SP, Fraser JL, Lu Z, Ogle ME, Wang JA, Wei L. Transplantation of hypoxia-preconditioned mesenchymal stem cells improves infarcted heart function via enhanced survival of implanted cells and angiogenesis. J Thorac Cardiovasc Surg. Apr. 2008;135(4):799-808. doi: 10.1016/j.jtcvs.2007.07.071. PMID: 18374759. (Exhibit 13).

Ishikawa K, Aguero J, Tilemann L, Ladage D, Hammoudi N, Kawase Y, Santos-Gallego CG, Fish K, Levine RA, Hajjar RJ. Characterizing preclinical models of ischemic heart failure: differences between LAD and LCx infarctions. Am J Physiol Heart Circ Physiol. Nov. 15, 2014;307(10):H1478-86. doi: 10.1152/ajpheart.00797.2013. Epub Sep. 12, 2014. PMID: 25217654; PMCID: PMC4233300. (Exhibit 14).

Jaski BE, Jessup ML, Mancini DM, Cappola TP, Pauly DF, Greenberg B, Borow K, Dittrich H, Zsebo KM, Hajjar RJ; Calcium Up-Regulation by Percutaneous Administration of Gene Therapy In Cardiac Disease (CUPID) Trial Investigators, Calcium upregulation by percutaneous administration of gene therapy in cardiac disease (CUPID Trial), a first-in-human phase 1/2 clinical trial. J Card Fail. Apr. 2009;15(3):171-81. doi: 10.1016/j.cardfail.2009.01.013. PMID: 19327618; PMCID: PMC2752875. (Exhibit 15).

Jessup M, Greenberg B, Mancini D, Cappola T, Pauly DF, Jaski B, Yaroshinsky A, Zsebo KM, Dittrich H, Hajjar RJ; Calcium Upregulation by Percutaneous Administration of Gene Therapy in Cardiac Disease (CUPID) Investigators. Calcium Upregulation by Percutaneous Administration of Gene Therapy in Cardiac Disease (CUPID): a phase 2 trial of intracoronary gene therapy of sarcoplasmic reticulum Ca2+-ATPase in patients with advanced heart failure. Circulation. Jul. 19, 2011;124(3):304-13. doi: 10.1161/CIRCULATIONAHA.111.022889. Epub Jun. 27, 2011. PMID: 21709064; PMCID: PMC5843948. (Exhibit 16).

Karantalis V, DiFede DL, Gerstenblith G, Pham S, Symes J, Zambrano JP, Fishman J, Pattany P, McNiece I, Conte J, Schulman S, Wu K, Shah A, Breton E, Davis-Sproul J, Schwarz R, Feigenbaum G, Mushtaq M, Suncion VY, Lardo AC, Borrello I, Mendizabal A, Karas TZ, Byrnes J, Lowery M, Heldman AW, Hare JM. Autologous mesenchymal stem cells produce concordant improvements in regional function, tissue perfusion, and fibrotic burden when administered to patients undergoing coronary artery bypass grafting: The Prospective Randomized Study of Mesenchymal Stem Cell Therapy in Patients Undergoing Cardiac Surgery (PROMETHEUS) trial. Circ Res. Apr. 11, 2014;114(8):1302-10. doi: 10.1161/CIRCRESAHA.114.303180. Epub Feb. 24, 2014. PMID: 24565698; PMCID: PMC4104798. (Exhibit 17).

Kim RJ, Wu E, Rafael A, Chen EL, Parker MA, Simonetti O, Klocke FJ, Bonow RO, Judd RM. The use of contrast-enhanced magnetic resonance imaging to identify reversible myocardial dysfunction. N Engl J Med. Nov. 16, 2000;343(20):1445-53. doi: 10.1056/NEJM200011163432003. PMID: 11078769. (Exhibit 18).

Liu JF, Wang BW, Hung HF, Chang H, Shyu KG. Human mesenchymal stem cells improve myocardial performance in a splenectomized rat model of chronic myocardial infarction. J Formos Med Assoc. Feb. 2008;107(2):165-74. doi: 10.1016/S0929-6646(08)60130-8. PMID: 18285249. (Exhibit 19).

Lu F, Zhao X, Wu J, Cui Y, Mao Y, Chen K, Yuan Y, Gong D, Xu Z, Huang S. MSCs transfected with hepatocyte growth factor or vascular endothelial growth factor improve cardiac function in the infarcted porcine heart by increasing angiogenesis and reducing fibrosis. Int J Cardiol. Sep. 10, 2013;167(6):2524-32. doi: 10.1016/j.ijcard.2012.06.052. Epub Sep. 13, 2012. PMID: 22981278. (Exhibit 20).

Jaroslav Meluzín, Jií Mayer, Ladislav Groch, Stanislav Janoušek, Ivan Horňáček, Ota Hlinomaz, Petr Kala, Roman Panovský, Jiří Prášek, Milan Kamínek, Jaroslav Staníček, Martin Klabusay, Zdenĕk Kořístek, Milan Navrátil, Ladislav Dušek, Jaroslava Vinklarková, Autologous transplantation of mononuclear bone marrow cells in patients with acute myocardial infarction: The effect of the dose of transplanted cells on myocardial function, American Heart Journal, vol. 152, Issue 5, 2006, pp. 975.e9-975.e15, ISSN 0002-8703. (Exhibit 21).

Noort WA, Oerlemans MI, Rozemuller H, Feyen D, Jaksani S, Stecher D, Naaijkens B, Martens AC, Bühring HJ, Doevendans PA, Sluijter JP. Human versus porcine mesenchymal stromal cells: phenotype, differentiation potential, immunomodulation and cardiac improvement after transplantation. J Cell Mol Med. Aug. 2012;16(8):1827-39. doi: 10.1111/j.1582-4934.2011.01455.x. PMID: 21973026; PMCID: PMC3822695. (Exhibit 22).

Paul D, Samuel SM, Maulik N. Mesenchymal stem cell: present challenges and prospective cellular cardiomyoplasty approaches for myocardial regeneration. Antioxid Redox Signal. Aug. 2009;11(8):1841-55. doi: 10.1089/ars.2009.2455. PMID: 19260767; PMCID: PMC2848514. (Exhibit 23).

Skalicka H, Horak J, Kobylka P, Palecek T, Linhart A, Aschermann M. Intracoronary injection of autologous bone marrow-derived mononuclear cells in patients with large anterior acute myocardial infarction and left ventricular dysfunction: a 24-month follow up study. Bratisl Lek Listy. 2012;113(4):220-7. doi: 10.4149/bll_2012_051. PMID: 22502753. (Exhibit 24).

Psaltis PJ, Paton S, See F, Arthur A, Martin S, Itescu S, Worthley SG, Gronthos S, Zannettino AC. Enrichment for STRO-1 expression enhances the cardiovascular paracrine activity of human bone marrow-derived mesenchymal cell populations. J Cell Physiol. May 2010;223(2):530-40. doi: 10.1002/jcp.22081. PMID: 20162565. (Exhibit 25).

(56) References Cited

OTHER PUBLICATIONS

Schuster MD, Kocher AA, Seki T, Martens TP, Xiang G, Homma S, Itescu S. Myocardial neovascularization by bone marrow angioblasts results in cardiomyocyte regeneration. Am J Physiol Heart Circ Physiol. Aug. 2004;287(2):H525-32. doi: 10.1152/ajpheart.00058. 2004. PMID: 15277196. (Exhibit 26).

Sievers B, Elliott MD, Hurwitz LM, Albert TS, Klem I, Rehwald WG, Parker MA, Judd RM, Kim RJ. Rapid detection of myocardial infarction by subsecond, free-breathing delayed contrast-enhancement cardiovascular magnetic resonance. Circulation. Jan. 16, 2007;115(2):236-44. doi: 10.1161/CIRCULATIONAHA.106. 635409. Epub Jan. 2, 2007. PMID: 17200443. (Exhibit 27).

Specifications Manual for Joint Commission National Quality Measures. (Exhibit 28).

Stone GW, Maehara A, Witzenbichler B, Godlewski J, Parise H, Dambrink JH, Ochala A, Carlton TW, Cristea E, Wolff SD, Brener SJ, Chowdhary S, El-Omar M, Neunteufl T, Metzger DC, Karwoski T, Dizon JM, Mehran R, Gibson Cm; Infuse-Ami Investigators. Intracoronary abciximab and aspiration thrombectomy in patients with large anterior myocardial infarction: the INFUSE-AMI randomized trial. JAMA. May 2, 2012;307(17):1817-26. doi: 10.1001/jama.2012.421. Epub Mar. 25, 2012. PMID: 22447888. (Exhibit 29).

Swynghedauw B. Molecular mechanisms of myocardial remodeling. Physiol Rev. Jan. 1999;79(1):215-62. doi: 10.1152/physrev. 1999.79.1.215. PMID: 9922372. (Exhibit 30).

Tatsumi T, Ashihara E, Yasui T, Matsunaga S, Kido A, Sasada Y, Nishikawa S, Hadase M, Koide M, Nakamura R, Irie H, Ito K, Matsui A, Matsui H, Katamura M, Kusuoka S, Matoba S, Okayama S, Horil M, Uemura S, Shimazaki C, Tsuji H, Saito Y, Matsubara H. Intracoronary transplantation of non-expanded peripheral blood-derived mononuclear cells promotes improvement of cardiac function in patients with acute myocardial infarction. Circ J. Aug. 2007;71(8):1199-207. doi: 10.1253/circj.71.1199. Erratum in: Circ J. Mar. 2014;78(3):777-9. PMID: 17652881. (Exhibit 31).

Mar. 1, 2019 Communication pursuant to Rule 114(2) EPC issued by the European Patent Office in connection with European Application No. 15822938.5. (Exhibit 32).

May 4, 2020 Communication pursuant to Rule 114(2) EPC issued by the European Patent Office in connection with European Application No. 1582293805. (Exhibit 33).

Aug. 1, 2022 Communication pursuant to Rule 114(2) EPC issued by the European Patent Office in connection with European Application No. 1582293805. (Exhibit 34).

Aug. 1, 2022 Communication pursuant to Rule 114(2) EPC issued by the European Patent Office in connection with European Application No. 1582293805. (Exhibit 35).

Trachtenberg B, Velazquez DL, Williams AR, McNiece I, Fishman J, Nguyen K, Rouy D, Altman P, Schwarz R, Mendizabal A, Oskouei B, Byrnes J, Soto V, Tracy M, Zambrano JP, Heldman AW, Hare JM. Rationale and design of the Transendocardial Injection of Autologous Human Cells (bone marrow or mesenchymal) in Chronic Ischemic Left Ventricular Dysfunction and Heart Failure Secondary to Myocardial Infarction (TAC-HFT) trial: A randomized, double-blind, placebo-controlled study of safety and efficacy. Am Heart J. Mar. 2011;161(3):487-93. doi: 10.1016/j.ahj.2010.11.024. PMID: 21392602. (Exhibit 36).

White HD, Norris RM, Brown MA, Brandt PW, Whitlock RM, Wild CJ. Left ventricular end-systolic vol. as the major determinant of survival after recovery from myocardial infarction. Circulation. Jul. 1987;76(1):44-51. doi: 10.1161/01.cir.76.1.44. PMID: 3594774. (Exhibit 37).

Williams AR, Hatzistergos KE, Addicott B, McCall F, Carvalho D, Suncion V, Morales AR, Da Silva J, Sussman MA, Heldman AW, Hare JM. Enhanced effect of combining human cardiac stem cells and bone marrow mesenchymal stem cells to reduce infarct size and to restore cardiac function after myocardial infarction. Circulation. Jan. 15, 2013;127(2):213-23. doi: 10.1161/CIRCULATIONAHA. 112.131110. Epub Dec. 5, 2012. PMID: 23224061; PMCID: PMC3579523. (Exhibit 38).

Wu Y, Chen L, Scott PG, Tredget EE. Mesenchymal stem cells enhance wound healing through differentiation and angiogenesis. Stem Cells. Oct. 2007;25(10):2648-59. doi: 10.1634/stemcells.2007-0226. Epub Jul. 5, 2007. PMID: 17615264. (Exhibit 39).

Wu E, Ortiz JT, Tejedor P, Lee DC, Bucciarelli-Ducci C, Kansal P, Carr JC, Holly TA, Lloyd-Jones D, Klocke FJ, Bonow RO. Infarct size by contrast enhanced cardiac magnetic resonance is a stronger predictor of outcomes than left ventricular ejection fraction or end-systolic volume index: prospective cohort study. Heart. Jun. 2008;94(6):730-6. doi: 10.1136/hrt.2007.122622. Epub Dec. 10, 2007. PMID: 18070953. (Exhibit 40).

Yang Z, Zhang F, Ma W, Chen B, Zhou F, Xu Z, Zhang Y, Zhang D, Zhu T, Wang L, Wang H, Ding Z, Zhang Y. A novel approach to transplanting bone marrow stem cells to repair human myocardial infarction: delivery via a noninfarct-relative artery. Cardiovasc Ther. Dec. 2010;28(6):380-5. doi: 10.1111/j.1755-5922.2009.00116. x. PMID: 20337639. (Exhibit 41).

Alan W. Heldman, et al. "Transendocardial Mesenchymal Stem Cells and Mononuclear Bone Marrow Cells for Ischemic Cardiomyopathy", JAMA: The Journal of the American Medical Association, Jan. 1, 2014, vol. 311, No. 1, pp. 62, US.

Barry Trachtenberg, et al., "Rationale and design of the Transendocardial Injection of Autologous Human Cells (bone marrow or mesenchymal) in Chronic Ischemic Left Centricular Dysfunction and Heart Failure Secondary to Myocardial Infarction (TAC-HFT) trial: A randomized, double-blind, placebo-controlled study of safety and efficacy", American Heart Journal, Nov. 25, 2010, vol. 161, No. 3, pp. 487-493, Mosby-Year Book Inc, US.

Fanglin Lu, et al., "MSCs transfected with hepatocyte growth factor or vascular endothelial growth factor improve cardiac function in the infarcted procine heart by increasing angiogenesis and reducing fibrosis", International Journal of Cardiology, Sep. 13, 2012, vol. 167, No. 6, pp. 2524-2532.

Tetsuya Tatsumi, et al., "Intracoronary transplantation of non-expanded peripheral blood-derived mononuclear cells promotes improvement of cardiac function in patients with acute myocardial infarction", Circulation Journal, Aug. 1, 2007, vol. 71, No. 8, pp. 1199-1207, Japanese Circulation Society, Kyoto, Japan.

Carolina Gandia, et al., "Human Dental Pulp Stem Cells Improve Left Ventricular Function, Induce Angiogenesis, and Reduce Infarct Size in Rats with Acute Myocardial infarction", Stem Cells, March 1, 2008, vol. 25, No. 3, pp. 638-645, US.

W. A. Noort, et al., "Human versus porcine mesenchymal stromal cells: phenotype, differentiation potential, immunomodulation and cardiac improvement after transplantation". J. Cell. Mol. Med., The Authors Journal of Cellular and Molecular Medicine, Jan. 1, 2012, vol. 16, No. 8, pp. 1827-1839, Blackwell Publishing Ltd.

International Search Report in connection with PCT International Application No. PCT/EP2015/081048.

Written Opinion of the International Searching Authority in connection with PCT International Application No. PCT/EP2015/081048.

Jul. 16, 2019 Communication Pursuant to Article 94 (3) EPC issued by the European Patent Office in connection with European Patent Application No. 15 822 938.5.

Yang et al., (2010), "A novel approach to transplanting bone marrow stem cells to repair human myocardial infarction: delivery via a noninfarct-relative artery", Cardiovascular Therapeutics, 28 (6) : 380-385, XP) 09514431, ISSN: 1755-5922.

Liu et al. (2008), "Human Mesenchymal Stem Cells Improve Myocardial Performance in a Splenectomized Rat Model of Chronic Myocardial Infarction" Journal of The Formosan Medical Association, Excerpta Medica Asia, Hong Kong, HK, 107 (2) : 165-174, XP025475345, ISN: 0929-6646, DPI: 10.1016/S0929-6646 (08) 60130-8.

Written Opinion issued Mar. 15, 2018 by the Intellectual Property Office of Singapore in connection with counterpart Singaporean Patent Application No. 11201704781X.

Chen, S. et al., Intracoronary transplantation of autologous bone marrow mesenchymal stem cells for ischemic cardiomyopathy due to isolated chronic occulated left anterior descending artery, J. Invasive Cardiol., Nov. 2006; 18 (11) : 552-6, abstract.

(56) References Cited

OTHER PUBLICATIONS

Paul, D. et al., "Mesenchymal Stem Cell: Present Challenges and Prospective Cellular Cardiomyoplasty Approaches for Myocardial Regeneration", Antioxidants & Redox Signaling, 2009, vol. 11, No. 8.

* cited by examiner

PREVENTION OF PROGRESSIVE HEART FAILURE

CROSS-REFERENCE TO RELATED APPLICATIONS

This application is a continuation of U.S. application Ser. No. 15/534,376, filed Jun. 8, 2017, now allowed, which is a § 371 national stage of PCT International Application No. PCT/EP2015/081048, filed Dec. 22, 2015, claiming priority of Australian Patent Application No. AU2014905240, filed Dec. 23, 2014, the contents of each of which are hereby incorporated by reference into the subject application.

TECHNICAL FIELD

The present disclosure relates to methods for preventing progressive heart failure in subjects with persistent left ventricular (LV) dysfunction. Such methods may also be used for treating or preventing progressive heart failure in subjects with a proximal left anterior descending (LAD) lesion and persistent left ventricular dysfunction.

BACKGROUND

Myocardial infarction (MI) is still one of the main causes of mortality and morbidity in developed countries. A recent update of US Medicare records was published that evaluated data involving 350,509 acute MI hospitalization in patients >65 years who were discharged alive after their event (Schuster et al. (2004) Physiol Heart Circa Physiol., 287(2): 525-32). Within the first year post the index event, 25.9% of the MI patients died with 50.5% re-hospitalized. In the month after a MI, the likelihood of death was 21 times higher and the likelihood of hospitalization and was 12 times higher than among the general Medicare-age population.

Patients who have larger infarcts post MI and more post-infarct LV dysfunction are at significantly increased risk of experiencing mid-to-long term cardiac events and death. Specifically, subjects having anterior wall infarets, larger infarets, and more LV dysfunction in the post-infarct period are at significantly increased risk of experiencing mid-to-long term cardiac events and death (Eitel et al. (2010) J Am Coll Cardiol., 55:2470-9).

An infarct due to proximal LAD occlusion continues to be a major risk factor for progressive LV dilatation, remodelling, and symptomatic progressive heart failure. In the post-angioplasty era, 3-year mortality post MI is still the highest for proximal LAD lesions (10% vs 3% for distal LAD) (Elsman et al. (2006) Am J Cardiol., 97(8):1137-41) and this is most likely due to the 40% greater infarct size associated with this anatomical lesion (Elsman et al. (2006) Am J Cardiol., 97(8):1137-41). Since infarct size >18.5% has been shown prospectively to result in a 30% incidence of Heart Failure-related Major Adverse Cardiac Events (HF-MACE, defined as heart failure hospitalization or death) over 2 years (Wu et al. (2008) Heart, 94:730-736), this suggests that a population of MI patients with proximal LAD lesions, low ejection fraction and large infarets is at the highest risk of subsequent HF-MACE.

Clearly, there is a need in the art for treating or preventing progressive heart failure.

SUMMARY

The present disclosure is based on the unexpected identification of a population of myocardial infarction (MI) subjects that respond well to stem cell therapy.

A large number of MI subjects with elevated troponin or CK-MB (>4×upper limits of normal (ULN)), a regional heart wall abnormality and, depressed global left ventricular systolic function (less than or equal 45% and greater than or equal to 20%) as determined on screening cardiac imaging performed within approximately 24 hours of the MI, were administered stem cell or placebo therapy shortly after MI.

The present inventors found that global left ventricular systolic function recovered to normal levels in a majority of these subjects approximately 5 days post MI. Administration of stem cell therapy provided no therapeutic improvement over placebo therapy in these subjects.

Surprisingly, administration of stem cell therapy provided a pronounced therapeutic improvement over placebo therapy in subjects who had proximal left anterior descending (LAD) arterial lesions. These results indicate that stem cell therapy may be useful for treating or preventing progressive heart failure in a sub-population of MI subjects, in particular, MI subjects with proximal LAD lesions.

Accordingly, in one example, the present disclosure provides a method of treating or preventing progressive heart failure in a myocardial infarction subject, the method comprising administering to the subject a population of mesenchymal lineage precursor or stem cells and/or progeny thereof and/or soluble factors derived therefrom, wherein the subject has a proximal left anterior descending (LAD) lesion.

In another example, the method comprises the steps of: i) selecting a subject having a proximal left anterior descending (LAD) lesion, and ii) administering to the subject a population of mesenchymal lineage stem or precursor cells and/or progeny thereof and/or soluble factors derived therefrom.

The present inventors also identified that the subjects with proximal LAD lesions that responded well to stem cell therapy also had persistent low ejection fraction approximately 5 days post MI. These results indicate that the methods of the present disclosure may also be useful for treating or preventing progressive heart failure in subjects with proximal LAD lesions and persistent low ejection fraction.

Accordingly, in another example, the present disclosure provides a method of treating progressive heart failure in a myocardial infarction subject, the method comprising administering to the subject a population of mesenchymal lineage precursor or stem cells and/or progeny thereof and/or soluble factors derived therefrom, wherein the subject has a proximal left anterior descending (LAD) lesion and has persistent left ventricular dysfunction.

In one example, the subject also has an elevated left ventricular end systolic volume (LVESV) of greater than 70 mL. In one example, the LVESV is greater than 80 mL, greater than 90 mL, greater than 100 mL, greater than 110 mL or greater than 120 mL. In another example, the LVESV is greater than 80 mL/m$^2$, greater than 90 mL/m$^2$, greater than 100 mL/m$^2$, greater than 110 mL/m$^2$, or greater than 120 mL/m$^2$.

In an example, the subject has a left ventricular ejection fraction (LVEF) of less than about 55%. In another example, the subject has a LVEF of less than about 45%. In another example, the subject has a LVEF of less than about 40%. In an example, the LVEF is measured via cardiovascular magnetic resonance imaging (cMR).

The present inventors have also identified that the timing of administration post MI may also benefit subjects. Thus, in an example, the mesenchymal lineage precursor or stem cells and/or progeny thereof and/or soluble factors derived therefrom are administered between about 1 and 7 days post-myocardial infarction. In an example, the mesenchymal lineage precursor or stem cells and/or progeny thereof and/or soluble factors derived therefrom are administered between about 2 and 7 days post-myocardial infarction. In another example, the mesenchymal lineage precursor or stem cells and/or progeny thereof and/or soluble factors derived therefrom are administered between about 3 and 5 days post-myocardial infarction.

The present inventors have further characterised the population of subjects that may benefit from the methods of the present disclosure based on the level of serum biomarkers relative to the upper limits of normal (ULM). In an example, the subject has greater than about 2× upper limit of normal creatine kinase-MB and/or troponin. In another example, the subject has greater than about 4× upper limit of normal creatine kinase-MB and/or troponin and/or myoglobin.

The present inventors have further characterised the population of subjects that may benefit from the methods of the present disclosure based on infarct size. In an example, the subject has an infarct size between about 10-25% of the left ventricle. In another example, the subject has an infarct size greater than about 18.5% of the left ventricle. In an example, infarct size is measured via cMR.

In another example, the methods of the present disclosure comprise administering a population of mesenchymal lineage precursor or stem cells enriched for STRO-1$^+$ cells and/or progeny thereof and/or soluble factors derived therefrom.

In another example, the methods of the present disclosure comprise administering a population of mesenchymal lineage precursor or stem cells enriched for STRO-1$^{bright}$ cells and/or progeny thereof and/or soluble factors derived therefrom.

In an example, the population of mesenchymal lineage precursor or stem cells express tissue non-specific alkaline phosphatase (TNAP) and/or the progeny cells and/or soluble factors are derived from mesenchymal lineage precursor or stem cells that express TNAP.

In an example, the population of mesenchymal lineage precursor or stem cells express angiopoietin-1 (Ang1) in an amount of at least 0.1 µg/$10^6$ cells and/or the progeny cells and/or soluble factors are derived from mesenchymal lineage precursor or stem cells that express Ang1 in an amount of at least 0.1 µg/$10^6$ cells. In an example, the population of mesenchymal lineage precursor or stem cells express Ang1 in an amount of at least 0.5 µg/$10^6$ cells. In an example, the population of mesenchymal lineage precursor or stem cells express Ang1 in an amount of at least 0.7 µg/$10^6$ cells. In an example, the population of mesenchymal lineage precursor or stem cells express Ang1 in an amount of at least 1 µg/$10^6$ cells.

In an example, the population of mesenchymal lineage precursor or stem cells express Vascular Endothelial Growth Factor (VEGF) in an amount less than about 0.05 µg/$10^6$ cells and/or the progeny cells and/or soluble factors are derived from mesenchymal lineage precursor or stem cells that express VEGF in an amount less than about 0.05 µg/$10^6$ cells and/or the progeny cells. In an example, the population of mesenchymal lineage precursor or stem cells express VEGF in an amount less than about 0.03 µg/$10^6$ cells.

In an example, the population of mesenchymal lineage precursor or stem cells express Ang1:VEGF at a ratio of at least about 2:1 and/or the progeny cells and/or soluble factors are derived from mesenchymal lineage precursor or stem cells that express Ang1:VEGF at a ratio of at least about 2:1. In an example, the population of mesenchymal lineage precursor or stem cells express Ang1:VEGF at a ratio of at least about 10:1. In an example, the population of mesenchymal lineage precursor or stem cells express Ang1:VEGF at a ratio of at least about 20:1. In an example, the population of mesenchymal lineage precursor or stem cells express Ang1:VEGF at a ratio of at least about 30:1.

In an example, the population of mesenchymal lineage precursor or stem cells and/or progeny thereof and/or soluble factors derived therefrom are administered systemically. In an example, the population of mesenchymal lineage precursor or stem cells and/or progeny thereof and/or soluble factors derived therefrom are administered intravenously, intramuscularly or intranasally. For example, the population of mesenchymal lineage precursor or stem cells and/or progeny thereof and/or soluble factors derived therefrom can be administered intravenously.

In an example, multiple doses of the population of mesenchymal lineage precursor or stem cells and/or progeny thereof and/or soluble factors derived therefrom are administered.

In an example, the methods of the present disclosure comprise administering between $1 \times 10^6$ to $8 \times 10^8$ cells. In an example, the methods of the present disclosure comprise administering between $1.2 \times 10^8$ to $4 \times 10^8$ cells. In an example, the methods of the present disclosure comprise administering at least about $1.5 \times 10^8$ cells.

In an example, the population of cells and/or progeny cells are autogeneic or allogeneic and/or the soluble factors are derived from autogeneic or alogeneic cells.

In an example, the population of cells and/or progeny thereof have been culture expanded prior to administration and/or prior to obtaining the soluble factors.

In an example, the mesenchymal lineage precursor or stem cells and/or progeny cells thereof and/or soluble factors derived therefrom are administered in the form of a composition comprising the mesenchymal lineage precursor or stem cells and/or progeny cells thereof and/or soluble factors derived therefrom and a carrier and/or excipient. For example, the composition may comprise a cryopreservative. Thus, in an example, the present disclosure relates to a population of mesenchymal lineage precursor or stem cells and/or progeny thereof and/or soluble factors derived therefrom for use in the treatment or prevention of progressive heart failure in a myocardial infarction (MI) subject, wherein the subject has a proximal left anterior descending (LAD) arterial lesion. In another example, the present disclosure relates to a use of a population of mesenchymal lineage precursor or stem cells and/or progeny thereof and/or soluble factors derived therefrom in the manufacture of a medicament for treating or preventing progressive heart failure in a myocardial infarction (MI) subject, wherein the subject has a proximal left anterior descending (LAD) arterial lesion. In these examples, the subject can have persistent left ventricular dysfunction. For example, the subject can have a LVEF of less than about 55%. In another example, the subject has a LVEF of less than about 45%. In another example, the subject has a LVEF of less than about 40%. In these examples, the mesenchymal lineage precursor or stem cells and/or progeny thereof and/or soluble factors derived therefrom can be administered between about 1 and 7 days post-myocardial infarction. For example, the mesenchymal lineage precursor or stem cells and/or progeny thereof and/or soluble factors derived therefrom are administered between about 3 and 5 days post-myocardial infarction. In these examples, the subject can ha greater than about 2× upper limit of normal creatine kinase-MB and/or troponin. In another example, the subject has greater than about 4× upper limit of normal creatine kinase-MB and/or troponin and/or myoglobin. In these examples, the subject can have an infarct size between about 10-25% of the left ventricle. In another example, the subject may have an infarct size greater than about 18.5% of the left ventricle. In these examples, the LVEF or infarct size may be measured via cMR.

DETAILED DESCRIPTION

General Techniques and Definitions

Figure 1:
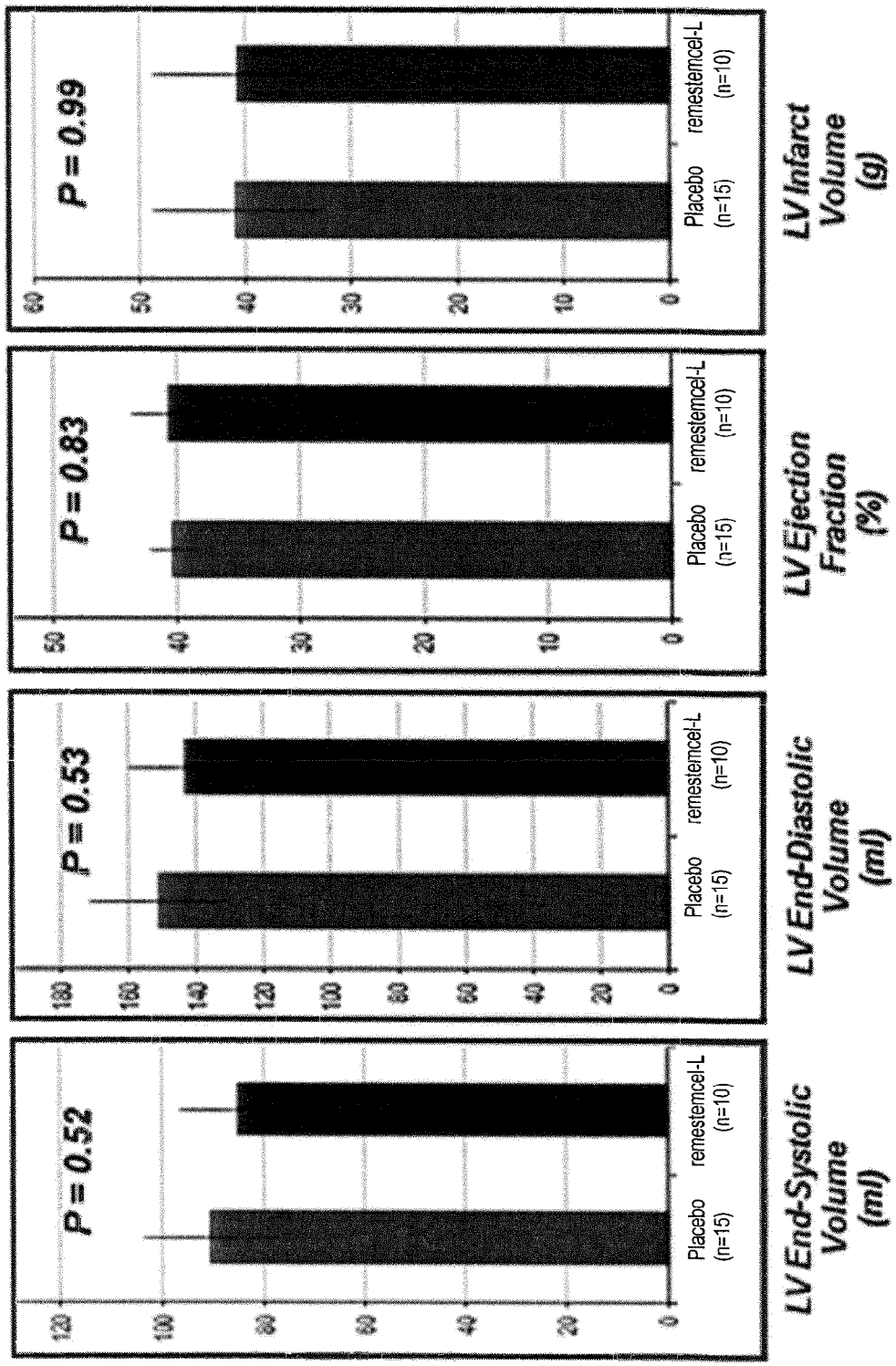
FIG. 1: Comparison of placebo and remestemcel-L treatment groups—Baseline.

Unless specifically defined otherwise, all technical and scientific terms used herein shall be taken to have the same meaning as commonly understood by one of ordinary skill in the art (e.g., in molecular genetics, molecular biology, cell culture, stem cell differentiation, immunology, immunohistochemistry, protein chemistry, and biochemistry).

Unless otherwise indicated, the stem cells, cell culture, and surgical techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The present disclosure is not to be limited in scope by the specific embodiments described herein, which are intended for the purpose of exemplification only. Functionally-equivalent products, compositions and methods are clearly within the scope of the disclosure, as described herein.

Any example disclosed herein shall be taken to apply mutatis mutandis to any other example unless specifically stated otherwise.

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Mesenchymal Lineage Precursor Cells

As used herein, the term "mesenchymal lineage precursor or stem cells" refers to undifferentiated multipotent cells that have the capacity to self renew while maintaining multipotentency and the capacity to differentiate into a number of cell types either of mesenchymal origin, for example, osteoblasts, chondrocytes, adipocytes, stromal cells, fibroblasts and tendons, or non-mesodermal origin, for example, hepatocytes, neural cells and epithelial cells. For the avoidance of doubt, a "mesenchymal lineage precursor cell" refers to a cell which can differentiate into a mesenchymal cell such as bone, cartilage, muscle and fat cells, and fibrous connective tissue.

The term "mesenchymal lineage precursor or stem cells" includes both parent cells and their undifferentiated progeny. The term also includes mesenchymal precursor cells, multipotent stromal cells, mesenchymal stem cells (MSCs), perivascular mesenchymal precursor cells, and their undifferentiated progeny.

Mesenchymal lineage precursor or stem cells can be autologous, xenogenic, syngenic or isogenic. Autologous cells are isolated from the same individual to which they will be reimplanted. Allogeneic cells are isolated from a donor of the same species. Xenogenic cells are isolated from a donor of another species. Syngenic or isogenic cells are isolated from genetically identical organisms, such as twins, clones, or highly inbred research animal models.

Mesenchymal lineage precursor or stem cells reside primarily in the bone marrow, but have also shown to be present in diverse host tissues including, for example, cord blood and umbilical cord, adult peripheral blood, adipose tissue, trabecular bone and dental pulp.

In one example the mesenchymal lineage precursor or stem cells are STRO-1+ mesenchymal precursor cells. As used herein, the phrase "STRO-1+ multipotential cells" shall be taken to mean STRO-1+ and/or TNAP+ progenitor cells capable of forming multipotential cell colonies.

STRO-1+ multipotential cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum; and are capable of differentiating into germ lines such as mesoderm and/or endoderm and/or ectoderm. Thus, STRO-1+ multipotential cells are capable of differentiating into a large number of cell types including, but not limited to, adipose, osseous, cartilaginous, elastic, muscular, and fibrous connective tissues. The specific lineage-commitment and differentiation pathway which these cells enter depends upon various influences from mechanical influences and/or endogenous bioactive factors, such as growth factors, cytokines, and/or local microenvironmental conditions established by host tissues.

Mesenchymal lineage precursor or stem cells can be isolated from host tissues and enriched for by selection of STRO-1+ cells. For example, a bone marrow aspirate from a subject may be further treated with an antibody to STRO-1 or TNAP to enable selection of mesenchymal lineage precursor or stem cells. In one example, the mesenchymal lineage precursor or stem cells can be enriched for by using the STRO-1 antibody described in (Simmons & Torok-Storb, 1991).

The terms "enriched", "enrichment" or variations thereof are used herein to describe a population of cells in which the proportion of one particular cell type or the proportion of a number of particular cell types is increased when compared with an untreated population of the cells (e.g., cells in their native environment). In one example, a population enriched for STRO-1+ cells comprises at least about 0.1% or 0.5% or 1% or 2% or 5% or 10% or 15% or 20% or 25% or 30% or 50% or 75% STRO-1+ cells. In this regard, the term "population of cells enriched for STRO-1+ cells" will be taken to provide explicit support for the term "population of cells comprising X % STRO-1+ cells", wherein X % is a percentage as recited herein. The STRO-1+ cells can, in some examples, form clonogenic colonies, e.g. CFU-F (fibroblasts) or a subset thereof (e.g., 50% or 60% or 70% or 70% or 90% or 95%) can have this activity.

In one example, the population of cells is enriched from a cell preparation comprising STRO-1+ cells in a selectable form. In this regard, the term "selectable form" will be understood to mean that the cells express a marker (e.g., a cell surface marker) permitting selection of the STRO-1+ cells. The marker can be STRO-1, but need not be. For example, cells (e.g., mesenchymal precursor cells) expressing STRO-2 and/or STRO-3 (TNAP) and/or STRO-4 and/or VCAM-1 and/or CD146 and/or 3G5 also express STRO-1 (and can be STRO-1bright). Accordingly, an indication that cells are STRO-1+ does not mean that the cells are selected by STRO-1 expression. In one example, the cells are selected based on at least STRO-3 expression, e.g., they are STRO-3+(TNAP+).

Reference to selection of a cell or population thereof does not necessarily require selection from a specific tissue source. As described herein STRO-1+ cells can be selected from or isolated from or enriched from a large variety of sources. That said, in some examples, these terms provide support for selection from any tissue comprising STRO-1+ cells (e.g., mesenchymal precursor cells) or vascularized tissue or tissue comprising pericytes (e.g., STRO-1+ pericytes) or any one or more of the tissues recited herein.

In one example, the mesenchymal lineage precursor or stem cells used in the present disclosure express one or more markers individually or collectively selected from the group consisting of TNAP+, VCAM-1+, THY-1+, STRO-2+, STRO-4+(HSP-90β), CD45+, CD146+, 3G5+ or any combination thereof.

By use of the term "individually" it is meant that the disclosure encompasses the recited markers or groups of markers separately, and that, notwithstanding that individual markers or groups of markers may not be separately listed herein the accompanying claims may define such marker or groups of markers separately and divisibly from each other.

By use of the term "collectively" it is meant that the disclosure encompasses any number or combination of the recited markers or groups of markers, and that, notwithstanding that such numbers or combinations of markers or groups of markers may not be specifically listed herein the accompanying claims may define such combinations or sub-combinations separately and divisibly from any other combination of markers or groups of markers.

In one example, the STRO-1+ cells are STRO-1$^{bright}$ (syn. STRO-1$^{bri}$). In another example, the STRO-1$^{bri}$ cells are preferentially enriched relative to STRO-1$^{dim}$ or STRO-1$^{intermediate}$ cells. In another example, the STRO-1$^{bri}$ cells are additionally one or more of TNAP+, VCAM-1+, THY-1+, STRO-2+, STRO-4+(HSP-90β) and/or CD146+. For example, the cells are selected for one or more of the foregoing markers and/or shown to express one or more of the foregoing markers. In this regard, a cell shown to express a marker need not be specifically tested, rather previously enriched or isolated cells can be tested and subsequently used, isolated or enriched cells can be reasonably assumed to also express the same marker.

In one example, the mesenchymal precursor cells are perivascular mesenchymal precursor cells as defined in WO 2004/85630, characterized by the presence of the perivascular marker 3G5.

A cell that is referred to as being "positive" for a given marker may express either a low (lo or dim) or a high (bright, bri) level of that marker depending on the degree to which the marker is present on the cell surface, where the terms relate to intensity of fluorescence or other marker used in the sorting process of the cells. The distinction of lo (or dim or dull) and bri will be understood in the context of the marker used on a particular cell population being sorted. A cell that is referred to as being "negative" for a given marker is not necessarily completely absent from that cell. This term means that the marker is expressed at a relatively very low level by that cell, and that it generates a very low signal when detectably labeled or is undetectable above background levels, e.g., levels detected using an isotype control antibody.

The term "bright" or "bri" as used herein, refers to a marker on a cell surface that generates a relatively high signal when detectably labeled. Whilst not wishing to be limited by theory, it is proposed that "bright" cells express more of the target marker protein (for example the antigen recognized by STRO-1) than other cells in the sample. For instance, STRO-1$^{bri}$ cells produce a greater fluorescent signal, when labeled with a FITC-conjugated STRO-1 antibody as determined by fluorescence activated cell sorting (FACS) analysis, than non-bright cells (STRO-1$^{dull/dim}$). In one example, "bright" cells constitute at least about 0.1% of the most brightly labeled bone marrow mononuclear cells contained in the starting sample. In other examples, "bright" cells constitute at least about 0.5%, at least about 1%, at least about 1.5%, or at least about 2%, of the most brightly labeled bone marrow mononuclear cells contained in the starting sample. In an example, STRO-1$^{bright}$ cells have 2 log magnitude higher expression of STRO-1 surface expression relative to "background", namely cells that are STRO-1-. By comparison, STRO-1$^{dim}$ and/or STRO-1$^{intermediate}$ cells have less than 2 log magnitude higher expression of STRO-1 surface expression, typically about 1 log or less than "background".

As used herein the term "TNAP" is intended to encompass all isoforms of tissue non-specific alkaline phosphatase. For example, the term encompasses the liver isoform (LAP), the bone isoform (BAP) and the kidney isoform (KAP). In one example, the TNAP is BAP. In one example, TNAP as used herein refers to a molecule which can bind the STRO-3 antibody produced by the hybridoma cell line deposited with ATCC on 19 Dec. 2005 under the provisions of the Budapest Treaty under deposit accession number PTA-7282.

Furthermore, in one example, the STRO-1+ cells are capable of giving rise to clonogenic CFU-F.

In one example, a significant proportion of the STRO-1+ multipotential cells are capable of differentiation into at least two different germ lines. Non-limiting examples of the lineages to which the multipotential cells may be committed include bone precursor cells; hepatocyte progenitors, which are multipotent for bile duct epithelial cells and hepatocytes; neural restricted cells, which can generate glial cell precursors that progress to oligodendrocytes and astrocytes; neuronal precursors that progress to neurons; precursors for cardiac muscle and cardiomyocytes, glucose-responsive insulin secreting pancreatic beta cell lines. Other lineages include, but are not limited to, odontoblasts, dentin-producing cells and chondrocytes, and precursor cells of the following: retinal pigment epithelial cells, fibroblasts, skin cells such as keratinocytes, dendritic cells, hair follicle cells, renal duct epithelial cells, smooth and skeletal muscle cells, testicular progenitors, vascular endothelial cells, tendon, ligament, cartilage, adipocyte, fibroblast, marrow stroma, cardiac muscle, smooth muscle, skeletal muscle, pericyte, vascular, epithelial, glial, neuronal, astrocyte and oligodendrocyte cells.

In an aspect of the present disclosure, the presently described mesenchymal lineage precursor or stem cells are MSCs. The MSCs may be a homogeneous composition or may be a mixed cell population enriched in MSCs. Homogeneous MSCs cell compositions may be obtained by culturing adherent marrow or periosteal cells, and the MSCs may be identified by specific cell surface markers which are identified with unique monoclonal antibodies. A method for obtaining a cell population enriched in MSCs is described, for example, in U.S. Pat. No. 5,486,359. Alternative sources for MSCs include, but are not limited to, blood, skin, cord blood, muscle, fat, bone, and perichondrium.

In another example, the mesenchymal lineage precursor or stem cells are CD29+, CD54+, CD73+, CD90+, CD102+, CD105+, CD106+, CD166+, MHC1+ MSCs (e.g. remestemcel-L).

Isolated or enriched mesenchymal lineage precursor or stem cells can be expanded in vitro by culture. Isolated or enriched mesenchymal lineage precursor or stem cells can be cryopreserved, thawed and subsequently expanded in vitro by culture.

In one example, isolated or enriched mesenchymal lineage precursor or stem cells are seeded at 50,000 viable cells/cm$^2$ in culture medium (serum free or serum-supplemented), for example, alpha minimum essential media (αMEM) supplemented with 5% fetal bovine serum (FBS) and glutamine, and allowed to adhere to the culture vessel overnight at 37° C., 20% O$_2$. The culture medium is subsequently replaced and/or altered as required and the cells cultured for a further 68 to 72 hours at 37° C., 5% O$_2$.

As will be appreciated by those of skill in the art, cultured mesenchymal lineage precursor or stem cells are phenotypically different to cells in vivo. For example, in one embodiment they express one or more of the following markers, CD44, NG2, DC146 and CD140b. Cultured mesenchymal lineage precursor or stem cells are also biologically different to cells in vivo, having a higher rate of proliferation compared to the largely non-cycling (quiescent) cells in vivo.

Mesenchymal lineage precursor or stem cells may also be cryopreserved prior to administration to a subject.

Expression of Ang1 and/or VEGF

The mesenchymal lineage precursor or stem cells of the present disclosure can be genetically modified or genetically unmodified and express high levels of Ang1. For example, the mesenchymal lineage precursor or stem cells can express Ang1 in an amount of at least 0.1 μg/10$^6$ cells. In other examples, the cells may express Ang1 in an amount of at least 0.2 μg/10$^6$ cells, 0.3 μg/10$^6$ cells, 0.4 μg/10$^6$ cells, 0.5 μg/10$^6$ cells, 0.6 μg/10$^6$ cells, 0.7 μg/10$^6$ cells, 0.8 μg/10$^6$ cells, 0.9 μg/10$^6$ cells, 1 μg/10$^6$ cells, 1.1 μg/10$^6$ cells, 1.2 g/10$^6$ cells, 1.3 μg/10$^6$ cells, 1.4 μg/10$^6$ cells, 1.5 μg/10$^6$ cells.

In another example, the mesenchymal lineage precursor or stem cells express VEGF in an amount less than about 0.05 μg/10$^6$ cells. In other examples, the cells express VEGF in an amount less than about 0.05 μg/10$^6$ cells, 0.04 μg/10$^6$ cells, 0.03 μg/10$^6$ cells, 0.02 μg/10$^6$ cells, 0.01 μg/10$^6$ cells, 0.009 μg/10$^6$ cells, 0.008 μg/10$^6$ cells, 0.007 μg/10$^6$ cells, 0.006 μg/10$^6$ cells, 0.005 μg/10$^6$ cells, 0.004 μg/10$^6$ cells, 0.003 μg/10$^6$ cells, 0.002 μg/10$^6$ cells, 0.001 μg/10$^6$ cells.

In another example, the mesenchymal lineage precursor or stem cells express Ang1:VEGF at a ratio of at least about 2:1. In other example, the cells express Ang1:VEGF at a ratio of at least about 10:1, 15:1, 20:1, 21:1, 22:1, 23:1, 24:1, 25:1, 26:1, 27:1, 28:1, 29:1, 30:1, 31:1, 32:1.

In an example, the mesenchymal lineage precursor or stem cells are genetically unmodified and express the above referenced levels of Ang-1 or VEGF or the above referenced Ang-1:VEGF ratios. As used herein, the term "genetically unmodified" refers to cells that have not been modified by transfection with a nucleic acid. For the avoidance of doubt, in the context of the present disclosure a mesenchymal lineage precursor or stem cell transfected with a nucleic acid encoding Ang1 would be considered genetically modified.

The amount of cellular Ang1 and/or VEGF that is expressed in a culture or present in a composition of mesenchymal lineage precursor or stem cells may be determined by various methods known to those skilled in the art. Such methods include, but are not limited to, Western blot, enzyme-linked immunosorbent assay (ELISA), fluorescence-linked immunosorbent assay (FLISA), competition assay, radioimmunoassay, lateral flow immunoassay, flow-through immunoassay, electrochemiluminescent assay, nephelometric-based assays, turbidometric-based assay, fluorescence activated cell sorting (FACS)-based assays for detection of Ang-1 or VEGF in culture medium used to culture mesenchymal lineage precursor cells or stem cells, and surface plasmon resonance (SPR or Biacore).

In one example the level of Ang1 and/or VEGF expressed by a culture or present in a composition of mesenchymal lineage precursor or stem cells is determined by an ELISA assay. For example, a cell lysate from a culture of mesenchymal lineage precursor or stem cells is added to a well of an ELISA plate. The well may be coated with a primary antibody, either a monoclonal or a polyclonal antibody(ies), against Ang1 or VEGF. The well is washed, and then contacted with a secondary antibody, either a monoclonal or a polyclonal antibody(ies), against the primary antibody. The secondary antibody is conjugated to an appropriate enzyme, such as horseradish peroxidase, for example. After an appropriate incubation period, the well is washed and then contacted with an appropriate substrate for the enzyme conjugated to the secondary antibody, such as one or more chromogens. Chromogens which may be employed include, but are not limited to, hydrogen peroxide and tetramethylbenzidine. After the substrate(s) is (are) added, the well is incubated for an appropriate period of time. Upon completion of the incubation, a "stop" solution is added to the well in order to stop the reaction of the enzyme with the substrate(s). The optical density (OD) of the sample then is measured. The optical density of the sample is correlated to the optical densities of samples containing known amounts of Ang1 or VEGF in order to determine the amount of Ang1 or VEGF expressed by the culture of mesenchymal lineage precursor or stem cells being tested. Methods for determining the Ang1:VEGF expression ratio will also be apparent to one of skill in the art. For example, after quantifying the levels of Ang1 and VEGF, a ratio based on the quantitated levels of Ang1 and VEGF could be represented as: (level of Ang1/level of VEGF)=Ang1:VEGF ratio.

Method of Treating Progressive Heart Failure

Heart failure occurs when the heart is unable to pump sufficiently to maintain blood flow to meet the needs of the body. One cause of heart failure is systolic dysfunction following a myocardial infarction (MI). A MI occurs when blood stops flowing properly to a part of the heart. The lack of blood supply results in a localized area of myocardial necrosis referred to as an infarct or infarction. The infarcted heart is unable to pump sufficiently to maintain blood flow to meet the needs of the body leading to multiple pathophysiologic responses and ultimately heart failure. Post MI, a series of compensatory mechanisms are initiated, serving to buffer the fall in cardiac output and assisting to maintain sufficient blood pressure to perfuse the vital organs. As a result, patients with heart failure may not progress for extended periods of time. However, the compensatory mechanisms eventually fail to compensate for the damaged heart, resulting in a progressive decline in cardiac output, termed "progressive heart failure". In the context of the present disclosure, the terms chronic heart failure, congestive heart failure, congestive cardiac failure, systolic dysfunction and advanced heart failure can be used interchangeably with "progressive heart failure".

The methods of the present disclosure relate to the treatment of the progressive decline in cardiac output characteristic of progressive heart failure. Accordingly, "treat" and "treatment", in the context of the present disclosure refers to both therapeutic treatment and prophylactic or preventative measures.

In an example, treatment reduces the chance or risk of heart failure-related Major Adverse Cardiac Events (HF-MACE) defined as a composite of cardiac related death or resuscitated cardiac death, or non-fatal decompensated heart failure events. In an example, the chance or risk of HF-MACE is reduced over at least 6 months, at least 12 months, at least 24 months, at least 36 months. In an example, treatment reduces the chance or risk of all-cause mortality.

Myocardial Infarction Subjects

The term "myocardial infarction (MI) subjects" is used to define subjects who have had a myocardial infarction. The methods of the present disclosure can be used to treat progressive heart failure in a specific population of MI subjects. Subjects in need of treatment include those already having progressive heart failure as well as those in which progressive heart failure is to be prevented, delayed or halted.

MI subjects treated with the methods of the present disclosure have a proximal left anterior descending (LAD) arterial lesion. As will be appreciated by one of skill in the art, the LAD artery travels in the anterior inter-ventricular groove that separates the right and the left ventricle, in the front of the heart. The diagonal (Dx) branch comes off the LAD and runs diagonally across the anterior wall towards its outer or lateral portion. Thus, the Dx supplies blood to the antero-lateral portion of the left ventricle. A subject may have one or several Dx branches. The first Dx branch serves as the boundary between the proximal and mid portion of the LAD. Thus, the portion of the artery prior to the origin of the Dx is known as the "proximal LAD", while the segment proximal to the first major side of the branch. The distal segment of the LAD is the terminal third of the artery.

In the context of the present disclosure the term "arterial lesion" encompasses an obstructive lesion, occluding the LAD of the heart or an arterial lesion that previously occluded the LAD that has been treated, for example, via percutaneous coronary intervention (PCI), also known as angioplasty.

In an example, a subject treated with the methods of the present disclosure received PCI within about 1 hour of ischemic symptoms. In other examples, the subject received PCI within about 2, about 3, about 4, about 5, about 6, about 7, about 8, about 9, about 10, about 11 hours of ischemic symptoms. In an example, the subject received PCI within about 12 hours of ischemic symptoms. In other examples, the subject received PCI within about 13, about 14, about 15, about 16, about 17, about 18, about 19, about 20 hours, about 21 hours, about 22 hours, about 23 hours or longer. Subjects being treated with thrombolytic therapy who have recurrent chest pain and/or ECG changes may not be transferred for PCI until at least 24 hours after onset of ischemic symptoms. Accordingly, in other examples, the subject received PCI within about 24 hours, about 25 hours, about 26 hours, about 27 hours, about 28 hours, about 29 hours, about 30 hours, about 35 hours, about 40 hours, about 48 hours of ischemic symptoms.

MI subjects can have elevated left ventricular end systolic volume (LVESV). In an example, a MI subject treated using the methods of the present disclosure has an elevated LVESV of greater than 70 mL. In an example, the subject has an elevated LVESV of greater than 80 mL, greater than 90 mL, greater than 100 mL, greater than 110 mL or greater than 120 mL. In another example, the s elevated LVESV of greater than 80 mL/m$^2$, greater than 90 mL/m$^2$, greater than 100 mL/m$^2$, greater than 110 mL/m$^2$, or greater than 120 mL/m$^2$.

MI can cause persistent left ventricular dysfunction. Thus, in another example, MI subject have a proximal LAD arterial lesion and persistent left ventricular dysfunction. Left ventricular dysfunction is characterised by a decrease in myocardial contractility. A reduction in the left ventricular ejection fraction (LVEF) results when myocardial contractility is decreased within the left ventricle. Thus, LVEF provides one way of determining left ventricular dysfunction.

LVEF and LVESV can be measured by a number of methods known in the art such as echocardiogram, Single Photon Emission Computed Tomography (SPECT) or cardio magnetic resonance imaging (cMRI).

In an example, a subject with a LVEF of less than about 60% has left ventricular dysfunction. In other examples, a subject with a LVEF of less than about 55%, 54%, 53%, 52%, 51%, 50%, 49%, 48%, 47%, 46% has left ventricular dysfunction. In another example, a subject with a LVEF of less than about 45% has left ventricular dysfunction. In other examples, a subject with a LVEF of less than about 44%, 43%, 42%, 41% has left ventricular dysfunction. In another example, a subject with a LVEF of less than about 40% has left ventricular dysfunction. In other examples, a subject with a LVEF of less than about 39%, 38%, 37%, 36%, 35%, 34%, 33%, 32%, 31%, 30% has left ventricular dysfunction.

In the context of the present disclosure the term "persistent left ventricular dysfunction" is used to define left ventricular dysfunction that persists over a period of time or series of measurements. For example, "persistent left ventricular dysfunction" can include left ventricular dysfunction that persists for between about 1 to about 14 days post MI or longer. For example, persistent left ventricular dysfunction can include left ventricular dysfunction that persists for between about 1 to about 10, between about 1 to about 9, between about 2 to about 8, between about 2 to about 7 days post MI. In another example, "persistent left ventricular dysfunction" can include left ventricular dysfunction that persists across about 1 to 10 measurements or more.

The size or amount of myocardial necrosis post MI is referred to clinically as the infarct size. The methods of the present disclosure relate to the treatment of MI subjects with large infarct size. For example, subjects treated using the methods of the present disclosure can have an infarct size greater than about 10-35% of the left ventricle. In other examples, subjects have an infarct size greater than about 11-34%, about 12-33%, about 13-32%, about 14-31%, about 15-30%, about 16-29%, about 17-28% of the left ventricle. In another example, subjects have an infarct size greater than about 18.5% of the left ventricle. In other examples, subjects have an infarct size greater than about 19-27%, about 20-26%, about 21-25%, about 22-24%, about 23% of the left ventricle.

Infarct size can be measured via a number of methods known in the art. Examples, of such methods include the use of serum markers such as creatine kinase (CK), CK-MB, troponin I, and brain natriuretic peptide troponin.

In an example, subjects treated with the methods of the present disclosure have troponin levels at least about 2× the upper limits of normal (ULM). In another example, subjects have troponin levels at least about 3×, about 4×, about 5×, about 6×ULM.

In an example, subjects treated with the methods of the present disclosure have creatine kinase-MB levels at least about 2×ULM. In another example, subjects have creatine kinase-MB levels at least about 3×, about 4×, about 5×, about 6×ULM.

Other examples of measuring infarct size include Sestamibi single-photon emission computed tomography (SPECT) myocardial perfusion imaging, magnetic resonance imaging. In one example, infarct size is measured using cMRI. Several cMRI techniques could be used for the diagnosis of infarct size. One of the most accurate and best validated is techniques is delayed enhancement cardio magnetic resonance imaging (DE-CMR). Thus, in an example, cMRI includes DE-CMR.

When the appropriate settings for DE-CMR are used, normal myocardium appears black or nulled, whereas non-viable regions appear bright or hyperenhanced. Accordingly, in an example infarct size can be determined by visual assessment of the bright an hyper enhanced regions. Other examples of determining infarct size are known in the art (Sievers et al. (2007), Circulation, 115, 236-244; Kim et al. (2000), N Engl J Med, 343, 1445-1453). In brief, hyperenhancement is scored on a 17-segment model with a 5-point scale for each segment (0=no hyperenhancement, 1% to 25%, 2=26% to 50%, 3=51% to 75%, 4=76% to 100%). Dark regions entirely encompassed within hyperenhanced myocardium are interpreted as regions of microvascular damage (no-reflow) and included as part of the infarct. Infarct size as percent LV myocardium is calculated by summing the regional scores, each weighted by the hyperenhancement range midpoint (i.e., 1=13%, 2=38%, 3=63%, 4=88%) and dividing by 17. In another example, infarct size can be quantified by planimetry of hyperenhanced areas on the stack of short-axis images.

In an example, infarct size is measured between about 1 and 40 days post MI. In other examples, infarct size is measured between about 1 and 40 days, between about 2 and 35 days, between about 3 and 30 days, between about 4 and 25 days, between about 5 and 20 days, between about 6 and 15 days post MI. For example, infarct size can be measured at about 30 days post MI.

In the context of the present disclosure "infarct size" refers to left ventricular infarct size. Put another way, left ventricular infarct size refers to the amount of the left ventricle that is infarcted.

The methods of the present disclosure can be used to treat progressive heart failure in a MI subject with various stages or classifications of heart failure. For example, the subject can have stage A, B, C or D heart failure. In an example, the subject has stage B or C heart failure. In these examples, heart failure staging is based on the American College of Cardiology (ACC) and the American Heart Association (AHA) staging criteria.

In another example, the subject can have Class I, II, III or IV heart failure. In an example, the subject has Class II or III heart failure. In these examples, heart failure classification is based on the New York Heart Association (NYHA) classification scale.

Cellular Compositions

In performing the methods of the present disclosure mesenchymal lineage precursor or stem cells can be administered in the form of a composition. In one example, such a composition comprises a pharmaceutically acceptable carrier and/or excipient.

The terms "carrier" and "excipient" refer to compositions of matter that are conventionally used in the art to facilitate the storage, administration, and/or the biological activity of an active compound (see, e.g., Remington's Pharmaceutical Sciences, 16th Ed., Mac Publishing Company (1980). A carrier may also reduce any undesirable side effects of the active compound. A suitable carrier is, for example, stable, e.g., incapable of reacting with other ingredients in the carrier. In one example, the carrier does not produce significant local or systemic adverse effect in recipients at the dosages and concentrations employed for treatment.

Suitable carriers for the present disclosure include those conventionally used, e.g., water, saline, aqueous dextrose, lactose, Ringer's solution, a buffered solution, hyaluronan and glycols are exemplary liquid carriers, particularly (when isotonic) for solutions. Suitable pharmaceutical carriers and excipients include starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like.

In another example, a carrier is a media composition, e.g., in which a cell is grown or suspended. Such a media composition does not induce any adverse effects in a subject to whom it is administered.

Exemplary carriers and excipients do not adversely affect the viability of a cell and/or the ability of a cell to reduce, prevent or delay progressive heart failure.

In one example, the carrier or excipient provides a buffering activity to maintain the cells and/or soluble factors at a suitable pH to thereby exert a biological activity, e.g., the carrier or excipient is phosphate buffered saline (PBS). PBS represents an attractive carrier or excipient because it interacts with cells and factors minimally and permits rapid release of the cells and factors, in such a case, the composition of the disclosure may be produced as a liquid for direct application to the blood stream or into a tissue or a region surrounding or adjacent to a tissue, e.g., by injection.

Stem cells and/or progeny cells thereof can also be incorporated or embedded within scaffolds that are recipient-compatible and which degrade into products that are not harmful to the recipient. These scaffolds provide support and protection for cells that are to be transplanted into the recipient subjects. Natural and/or synthetic biodegradable scaffolds are examples of such scaffolds.

A variety of different scaffolds may be used successfully in the practice of the disclosure. Exemplary scaffolds include, but are not limited to biological, degradable scaffolds. Natural biodegradable scaffolds include collagen, fibronectin, and laminin scaffolds. Suitable synthetic material for a cell transplantation scaffold should be able to support extensive cell growth and cell function. Such scaffolds may also be resorbable. Suitable scaffolds include polyglycolic acid scaffolds, (e.g., as described by Vacanti, et al. J. Ped. Surg. 23:3-9 1988; Cima, et al. Biotechnol. Bioeng. 38:145 1991; Vacanti, et al. Plast. Reconstr. Surg. 88:753-9 1991); or synthetic polymers such as polyanhydrides, polyorthoesters, and polylactic acid.

In another example, the cells may be administered in a gel scaffold (such as Gelfoam from Upjohn Company).

The cellular compositions described herein may be administered alone or as admixtures with other cells. The cells of different types may be admixed with a composition of the disclosure immediately or shortly prior to administration, or they may be co-cultured together for a period of time prior to administration.

In one example, the composition comprises an effective amount or a therapeutically or prophylactically effective amount of cells. For example, the composition comprises about $1\times10^5$ cells to about $1\times10^9$ cells or about $1.25\times10^3$ cells to about $1.25\times10^7$ cells. The exact amount of cells to be administered is dependent upon a variety of factors, including the age, weight, and sex of the subject, and the extent and severity of the disorder being treated.

Exemplary dosages include at least about $1.2\times10^8$ to about $8\times10^{10}$ cells, such as between about $1.3\times10^8$ to about $8\times10^9$ cells, about $1.4\times10^8$ to about $8\times10^8$ cells, about $1.5\times10^8$ to about $7.2\times10^8$ cells, about $1.6\times10^8$ to about $6.4\times10^8$ cells, about $1.7\times10^8$ to about $5.6\times10^8$ cells, about $1.8\times10^8$ to about $4.8\times10^8$ cells, about $1.9\times10^8$ to about $4.0\times10^8$ cells, about $2.0\times10^8$ to about $3.2\times10^8$ cells, about $2.1\times10^8$ to about $2.4\times10^8$ cells. For example, a dose can include at least about $1.5\times10^8$ cells. For example, a dose can include at least about $2.0\times10^8$ cells.

Put another way, exemplary doses include at least about $1.5\times10^6$ cells/kg (80 kg subject). In an example, a dose can include at least about $2.5\times10^6$ cells/kg. In other examples, a dose can comprise between about $1.5\times10^6$ to about $1\times10^9$ cells/kg, about $1.6\times10^6$ to about $1\times10^8$ cells/kg, about $1.8\times10^6$ to about $1\times10^6$ cells/kg, about $1.9\times10^6$ to about $9\times10^6$ cells/kg, about $2.0\times10^6$ to about $8\times10^6$ cells/kg, about $2.1\times10^6$ to about $7\times10^6$ cells/kg, about $2.3\times10^6$ to about $6\times10^6$ cells/kg, about $2.4\times10^6$ to about $5\times10^6$ cells/kg, about $2.5\times10^6$ to about $4\times10^6$ cells/kg, about $2.6\times10^6$ to about $3\times10^6$ cells/kg.

In an example, the mesenchymal lineage precursor or stem cells comprise at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99% of the cell population of the composition.

Compositions of the disclosure may be cryopreserved. Cryopreservation of mesenchymal lineage precursor or stem cells can be carried out using slow-rate cooling methods or 'fast' freezing protocols known in the art. Preferably, the method of cryopreservation maintains similar phenotypes, cell surface markers and growth rates of cryopreserved cells in comparison with unfrozen cells.

The cryopreserved composition may comprise a cryopreservation solution. The pH of the cryopreservation solution is typically 6.5 to 8, preferably 7.4.

The cyropreservation solution may comprise a sterile, non-pyrogenic isotonic solution such as, for example, PlasmaLyte A™. 100 mL of PlasmaLyte A™ contains 526 mg of sodium chloride, USP (NaCl); 502 mg of sodium gluconate ($C_6H_{11}NaO_7$); 368 mg of sodium acetate trihydrate, UISP ($C_2H_3NaO_2\cdot3H_2O$); 37 mg of potassium chloride, USP (KCl); and 30 mg of magnesium chloride, USP ($MgCl_2\cdot6H_2O$). It contains no antimicrobial agents. The pH is adjusted with sodium hydroxide. The pH is 7.4 (6.5 to 8.0).

The cryopreservation solution may comprise Profreeze™. The cryopreservation solution may additionally or alternatively comprise culture medium, for example, αMEM.

To facilitate freezing, a cryoprotectant such as, for example, dimethylsulfoxide (DMSO), is usually added to the cryopreservation solution. Ideally, the cryoprotectant should be nontoxic for cells and patients, nonantigenic, chemically inert, provide high survival rate after thawing and allow transplantation without washing. However, the most commonly used cryoprotector, DMSO, shows some cytotoxicity. Hydroxylethyl starch (HES) may be used as a substitute or in combination with DMSO to reduce cytotoxicity of the cryopreservation solution.

The cryopreservation solution may comprise one or more of DMSO, hydroxyethyl starch, human serum components and other protein bulking agents. In one example, the cryopreserved solution comprises about 5% human serum albumin (HSA) and about 10% DMSO. The cryopreservation solution may further comprise one or more of methylcellulose, polyvinyl pyrrolidone (PVP) and trehalose.

In one embodiment, cells are suspended in 42.5% Profreeze™/50% αMEM/7.5% DMSO and cooled in a controlled-rate freezer.

The cryopreserved composition may be thawed and administered directly to the subject or added to another solution, for example, comprising HA. Alternatively, the cryopreserved composition may be thawed and the mesenchymal lineage precursor or stem cells resuspended in an alternate carrier prior to administration.

In an example, the cellular compositions described herein may be administered between about 1 and about 10 days post MI. In other examples, the cellular compositions described herein may be administered between about 1 and 9 days, between about 1 and 8 days, between about 2 and 7 days, between about 2 and 6 days, between about 3 and 5 days post MI. For example, the cellular compositions described herein may administered about 5 days post MI In an example, the cellular compositions described herein may be administered between about 1 and about 10 days post PCI. In other examples, the cellular compositions described herein may be administered between about 1 and 9 days, between about 1 and 8 days, between about 2 and 7 days, between about 2 and 6 days, between about 3 and 5 days post PCI. For example, the cellular compositions described herein may administered about 5 days post PCI In an example, the cellular compositions described herein may be administered as a single dose. In another example, cellular compositions are administered over multiple doses. For example, at least 2, at least 3, at least 4, at least 5, at least 6, at least 7, at least 8, at least 9, at least 10 doses.

In one example, mesenchymal lineage precursor or stem cells can be culture expanded prior to administration. Various methods of mesenchymal lineage precursor or stem cell culture are known in the art. In an example, mesenchymal lineage precursor or stem cells are culture expanded in a serum free medium prior to administration.

The mesenchymal lineage precursor or stem cells may be administered systemically, such as, for example, by intravenous, intraarterial, or intraperitoneal administration. The mesenchymal lineage precursor or stem cells may also be administered by intranasal, intramuscular or intracardiac administration. In an example, the mesenchymal lineage precursor or stem cells are administered directly into the myocardium. For example, the mesenchymal lineage precursor or stem cells can be administered directly into the myocardium of the left ventricle. In an example, the mesenchymal lineage precursor or stem cells are administered via an endomyocardial catheter such as the J&J Myostar™ injection catheter.

In an example, the mesenchymal lineage precursor or stem cells are administered to viable myocardium. In an example, the mesenchymal lineage precursor or stem cells are administered to hibernating myocardium. One of skill in the art would be able to identify viable and/or hibernating myocardium using methods known in the art. For example, a mapping catheter system such as the NOGASTAR™ Mapping Catheter system can be used to identify viable and/or hibernating myocardium.

In another example, the mesenchymal lineage precursor or stem cells are administered via intracoronary infusion. For example, mesenchymal lineage precursor or stem cells can be administered into the left anterior descending (LAD) artery. In an example, mesenchymal lineage precursor or stem cells are administered into the LAD artery immediately after LAD revascularisation via PCI.

In an example, cells are contained within a chamber that does not permit the cells to exit into a subject's circulation, however that permits factors secreted by the cells to enter the circulation. In this manner soluble factors may be administered to a subject by permitting the cells to secrete the factors into the subject's circulation. Such a chamber may equally be implanted at a site in a subject to increase local levels of the soluble factors, e.g., implanted in or near the heart.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The present application claims priority from AU 2014905240 filed 23 Dec. 2014, the disclosures of which are incorporated herein by reference.

EXAMPLES

Example 1

Clinical Phase 2A/2b IV MSC's in AMI

A randomized placebo-controlled Phase 2a/2b trial was initiated to evaluate a single intravenous (IV) dose of 200 million mesenchymal stem cells (MSCs) administered at 2-7 days in patients with ST elevation MI (STEMI) or Non-ST elevation myocardial infarction (NSTEMI) and a reduced cardiac ejection fraction.

A Phase IIa/IIb, multicentre, randomized, double-blind, placebo-controlled study was designed to evaluate the safety and efficacy of remestemcel-L (ex-vivo cultured adult human mesenchymal stem cells) intravenous infusion following acute myocardial infarction.

The study was a Phase ii, multicentre, randomized, double-blind, placebo-controlled study of 220 subjects who had recently experienced an acute myocardial infarction (MI). Acute MI patients eligible for this study included those patients with any acute coronary syndrome resulting in:

1) positive biomarkers (troponin or CK-MB>4×ULN);
2) a regional wall motion abnormality;
3) a depressed global left ventricular systolic function≤45% and ≥20% as determined on screening cardiac imaging which was performed within approximately 24 hours after the initial onset of the acute event.

Subjects were evaluated for safety and efficacy until death, withdrawal, or 60 months after investigational agent (IA) infusion, whichever occurred first. The treatment window was 2 to 7 days after initial onset of acute MI.

Subjects were randomized to the placebo or the treatment group (remestemcel-L 200×10$^6$ cells per infusion). Approximately equal numbers of subjects in each cohort were assigned to each of the 2 groups (1:1 randomization).

Overall Study Data Through Month 24

Overall, intravenous mesenchymal stem cell (MSC) therapy was well tolerated and the study demonstrated that use of IV MSC at the time of an acute myocardial infarct was safe. There were no evident differences between remestemcel-L and placebo in overall adverse events (90.9% vs. 90.9%) and serious adverse events (32.7% vs. 33.6%) in acute MI subjects. There were 5 deaths in the study: 2 in the remestemcel-L group, 3 in the placebo group. Only 1 subject death was considered possibly related to study treatment, and that subject received placebo.

Although in the original study design the principal inclusion criterion for study entry was an LVEF <45% determined by cardiac imaging approximately 24 hours post the acute event, over 70% of the subjects that qualified at screening were actually found to have an LVEF >45% by cMR shortly prior to the intravenous administration of study product, which was administered at a mean time point of 5.4 days post MI. This is most likely due to the natural course of myocardial recovery after an MI and angioplasty procedure. Therefore, less than 30% of enrolled patients actually met the study design criteria of persistent left ventricular (LV) dysfunction at the time of remestemcel-L infusion, and consequently most patients in this study actually had normal LV function by the time they received treatment.

66 patients had left anterior descending (LAD) lesions with low ejection fraction at screening. For the primary efficacy variable of cMR derived change in left ventricular end systolic volume at 3 months, subjects in the remestemcel-L group exhibited numerical, but non-statistically significant changes (+3.31 mL vs. −0.35, p=0.17). Similar non-significant, numeric changes were also evident at 6 months in ESV, as well as in mean infarct size and ejection fraction.

The effects of remestemcel-L therapy were then evaluated in the subset of patients with persistent LV dysfunction and proximal LAD lesions as measured by cMR just prior to infusion.

Post-Hoc Efficacy Analysis

The central rationale for this study was that remestemcel-L would be effective in those post MI patients with persistent LV dysfunction. However, in the overall patient population over 70% had normalized their ejection fraction between selection for trial inclusion at 24 hours post MI and treatment infusion at day 2-7 (mean treatment administration at day 5.4). This may reflect early recovery of stunned myocardium within days post reperfusion with PCI resulting in improved LV systolic function prior to treatment administration. The disparity in LVEF data between study entry and treatment administration significantly negated the original trial's ability to adequately test the study's underlying hypothesis.

Consequently, a post hoc analysis was designed and intended to further investigate the potential effect of remestemcel-L on the subset of patients who would be expected to have the most extensive disease post MI, specifically subjects with proximal LAD culprit lesions and cMR LVEF ≤45% at the time of treatment administration.

Post-hoc analysis was designed to answer whether in patients with the highest risk of progressive heart failure a single dose ($200 \times 10^6$ cells) of intravenously administered MSCs would be more effective than placebo for reversal of left ventricular heart failure and the prevention of progressive adverse LV remodeling at 6 months post the index AMI. The highest risk patients were selected for study entry as follows:

A first time anterior wall acute myocardial infarction due to a proximal LAD culprit lesion;

The culprit coronary artery lesion was successfully treated with a PCI procedure within 12 hours of the onset of ischemic symptoms;

Persistent L V systolic dysfunction (i.e., post-PCI LVEF <45% by cMR) present 2-7 days after the index AMI.

Of the 220 patients randomized into the overall trial a total of 25 subjects fulfilled the criteria consisting of an MI localized to the proximal LAD, ischemic time of <12 hours, a successful Percutaneous Coronary Intervention (PCI), a baseline cMR LVEF <45%, and treatment with investigational product between 2 and 7 days post the index AMI.

These 25 subjects constituted the evaluation population for the post hoc analysis and were distributed as 10 subjects in the remestemcel-L group and 15 subjects in the placebo group. In the post hoc analysis performed for the Phase 2 remestemcel-L AMI trial, a responder index approach was used to assess the effects of cell therapy on adverse LV remodelling. This approach was used to assess the post-hoc study's primary endpoint in which evaluations of LVESV change from baseline were conducted to determine if a clinically meaningful difference was present at 6 months post AMI between patients treated with remestemcel-L compared to placebo.

It has been shown previously that of the commonly evaluated measurements of LV systolic function, LVESV is a strong predictor of long term survival after recovery from an acute myocardial infarction (White et al. (1987) Circulation, 76:44-51).

Indeed, it is now well accepted that LVESV is a useful surrogate efficacy endpoint of biologically and clinically meaningful change as it relates to the development of adverse LV remodelling and associated MACE in patients at risk for the development/progression of LV systolic function related heart failure. This analysis model has been shown to correlate well with MACE outcomes in a Phase 2 gene therapy trial (Hajjar et al. (2008) J Card Fail., 14(5):355-67; Jaski et al. (2009) Card Fail., 15(3):171-81; Jessup et al. (2011) Circulation, 124:304-313).

In the current analysis of primary and secondary endpoints, a treatment responder was defined using pre-specified threshold boundaries for success. These values calculated as 6 Month minus baseline data were utilized to ensure that the interval change was both outside the range of usual measurement error and potentially clinically significant.

| Parameter | Responder Boundary |
| --- | --- |
| LVESV | ≤−10 mL |
| LVEDV | <+10 mL |
| LVEF | ≥+5 LVEF units |
| LV Infarct Volume | ≤−10 g |

Efficacy Results of Post Hoc Population

At baseline, there were no significant differences between treatment groups for LVESV, LVEDV, LVEF or LV infarct volume. However, interesting trends were evident within the change from baseline data for the 6 month follow-up visit.

LV Infarct Volume:

At baseline, mean infarct volumes between the placebo and the remestemcel-L group were similar and very high, 40.9+13.75 g (mean+SD) and 40.76+17.82 g (mean+SD), respectively. Assuming a total mean myocardial mass of approximately 130 g in these patients (Stone et al. (2012) JAMA., 307:17, 1817-26), these values represent a very high risk population with approximately 30% infarct sizes at the time of therapeutic intervention. Since infarct size >18.5% has been shown prospectively to result in a 30% incidence of heart failure-related Major Adverse Cardiac Events (HF-MACE, defined as heart failure hospitalization or death) over 2 years, this confirms that the population of AMI patients evaluated in this post-hoc analysis were at highest risk for subsequent HF-MACE.

At the end of 6 months, subjects in the remestemcel-L group exhibited a decrease in LV infarct volume from a baseline value of 40.76+17.82 g to 26.6+12.94 g (mean+SD). This represented a −14.14+13.94 g change. By contrast, placebo subjects showed a nominally smaller decrease in LV infarct volume from a baseline value of 40.9+13.75 g (mean+SD) to 31.59+12.70 g. This represented a −7.74+10.84 g change. The placebo corrected difference was −6.40 g (p=0.187).

These results indicate that remestemcel-L enhanced the natural endogenous healing process of infarct volume reduction by two-fold over 6 months relative to placebo, from approximately 30% infarct size at baseline to approximately 20% infarct size (assuming a mean LV mass of 130 g) at 6 months.

LVESV:

At the end of 6 months, subjects in the remestemcel-L group exhibited decreases in LVESV from a baseline value of 85.0+15.89 mL to 73.0+24.24 mL (mean+SD). This represented a −12.0+16.57 mL change. By contrast, placebo subjects showed an increase in LVESV from a baseline value of 90.5+23.54 mL (mean+SD) to 92.8+35.40 mL. This represented a 2.2+28.53 mL change. The placebo corrected difference was −14.2 mL (p=0.174).

Summary of LV End Systolic Volume at Baseline and 6 Months Post- Treatment (LOCF Analysis)

|  | BASELINE | 6 MONTHS | CHANGE |
| --- | --- | --- | --- |
| REMESTEMCEL-L |  |  |  |
| N | 10 | 10 | 10 |
| Mean ± SD | 85.0 ± 15.9 | 73.0 ± 24.2 | −12.0 ± 16.6 |
| Median | 86.5 | 71.2 | −10.9 |
| Minimum, Maximum | 59, 115 | 39, 121 | −43.7 |
| PLACEBO |  |  |  |
| N | 15 | 15 | 15 |
| Mean ± SD | 90.5 ± 23.5 | 92.8 ± 35.4 | 2.2 ± 28.5 |
| Median | 85.8 | 89.0 | −6.1 |
| Minimum, Maximum | 43, 139 | 36, 180 | −34.74 |
| p-value*: | 0.520 |  | 0.174 |
| REMESTEMCEL-L vs. PLACEBO |  |  |  |

*Baseline Treatment comparison using ANOVA. Other treatment comparisons using ANCOVA with treatment as fixed effect and baseline as a covariate
Source: Table 14.2.17.S.1

Notably, a change in infarct size from approximately 30% at baseline to approximately 20% at 6 months (assuming a mean LV mass of 130 g), as was seen in the remestemcel-L group, would be expected to reduce LVESV by at least 10 mL (Wu et al. (2007) Stem Cells, 25:26, 48-59) over this period; our results are consistent and confirm the concordance of our dataset.

LVEDV:

At the end of 6 months, subjects in the remestemcel-L group exhibited an increase in LVEDV from a baseline value of 142.9+24.01 mL to 154.4+37.52 mL (mean+SD). This represented a 11.5+27.91 mL change. By contrast, placebo subjects showed an increase in LVEDV from a baseline value of 151.2+35.98 mL (mean+SD) to 167.8+41.66 mL. This represented a 16.6+27.30 mL change. The placebo corrected difference was −5.1 mL (p=0.618).

Figure 2:
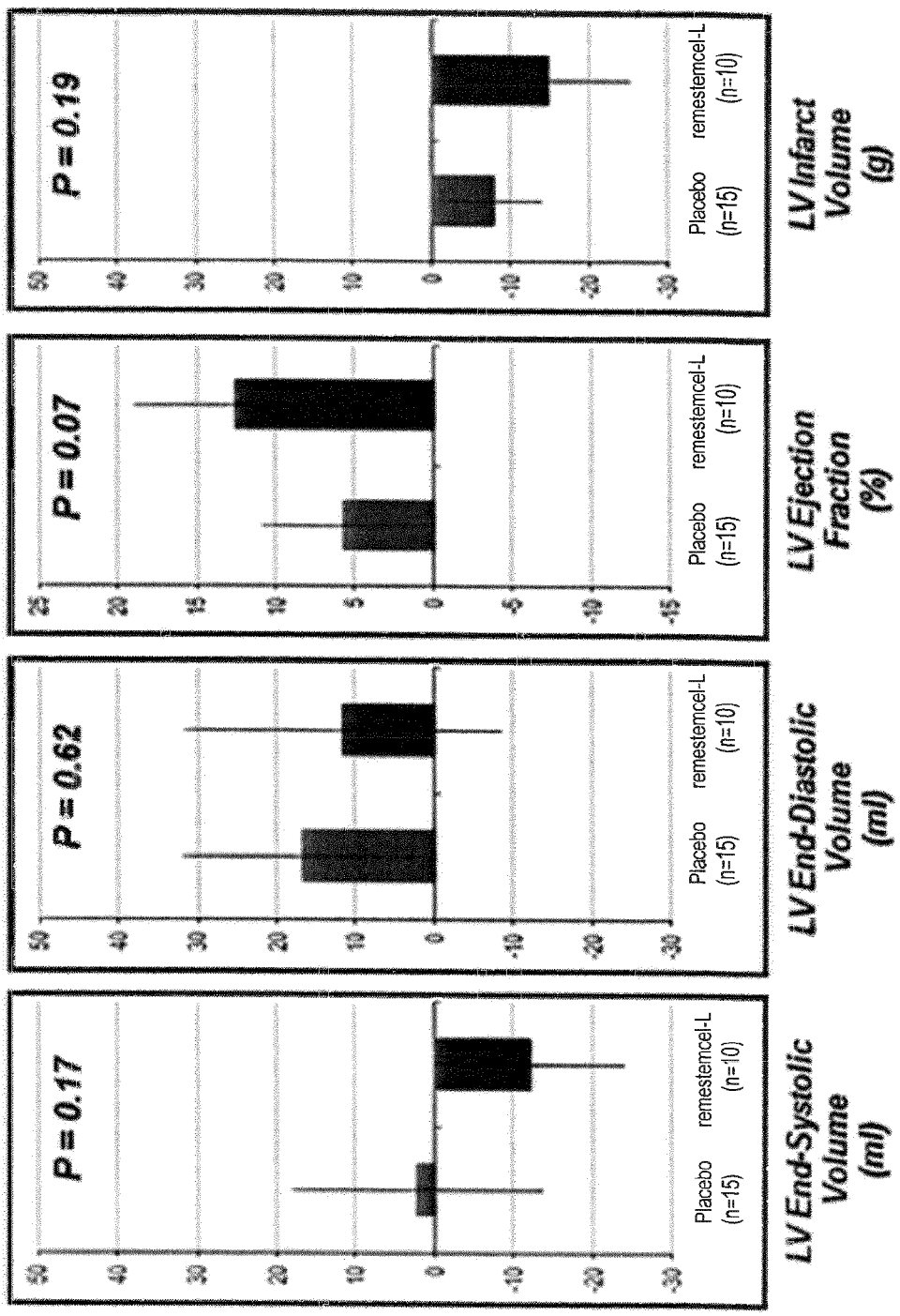
FIG. 2: Comparison of placebo and remestemcel-L treatment groups—Month 6 Change from base line.

LVEF:

At the end of 6 months, subjects in the remestemcel-L group exhibited an increase in LVEF from a baseline value of 40.6+4.23% to 53.1+8.71% (mean+SD). This represented a 12.5+8.88 LVEF unit change. By contrast, placebo subjects showed a nominally smaller increase in LVEF from a baseline value of 40.3+3.47% (mean+SD) to 45.8+9.08%. This represented a 5.6+9.48 LVEF unit change. The placebo corrected difference was 6.9 LVEF units (p=0.066) (See FIGS. 1 and 2).

Summary of LV Ejection Fraction at Baseline and 6 Months Post- Treatment (LOCF Analysis)

|  | BASELINE | 6 MONTHS | CHANGE |
| --- | --- | --- | --- |
| REMESTEMCEL-L |  |  |  |
| N | 10 | 10 | 10 |
| Mean ± SD | 40.6 ± 4.2 | 53.1 ± 8.7 | 12.5 ± 8.9 |
| Median | 41.9 | 52.0 | 13.7 |
| Minimum, Maximum | 34, 45 | 41, 66 | −3, 26 |
| PLACEBO |  |  |  |
| N | 15 | 15 | 15 |
| Mean ± SD | 40.3 ± 3.5 | 45.8 ± 9.1 | 5.6 ± 9.5 |
| Median | 40.3 | 44.6 | 4.5 |
| Minimum, Maximum | 33, 45 | 29, 58 | −14, 19 |
| p-value*: | 0.832 |  | 0.066 |
| REMESTEMCEL-L vs. PLACEBO |  |  |  |

*Baseline Treatment comparison using ANOVA. Other treatment comparisons using ANCOVA with treatment as fixed effect and baseline as a covariate Source: Table 14.2.19.S.1

Responder Analysis

Figure 3:
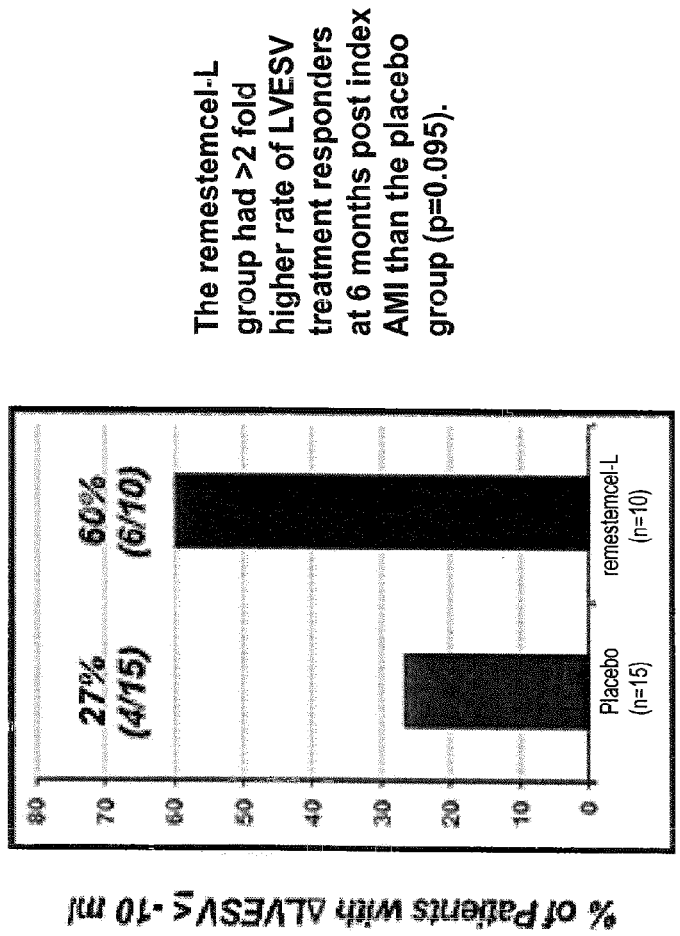
FIG. 3: Comparison of placebo and remestemcel-L treatment groups—% of patients with a change in left ventricular end diastolic volume less than −10 ml after month 6. Change measured from base line.
Figure 4:
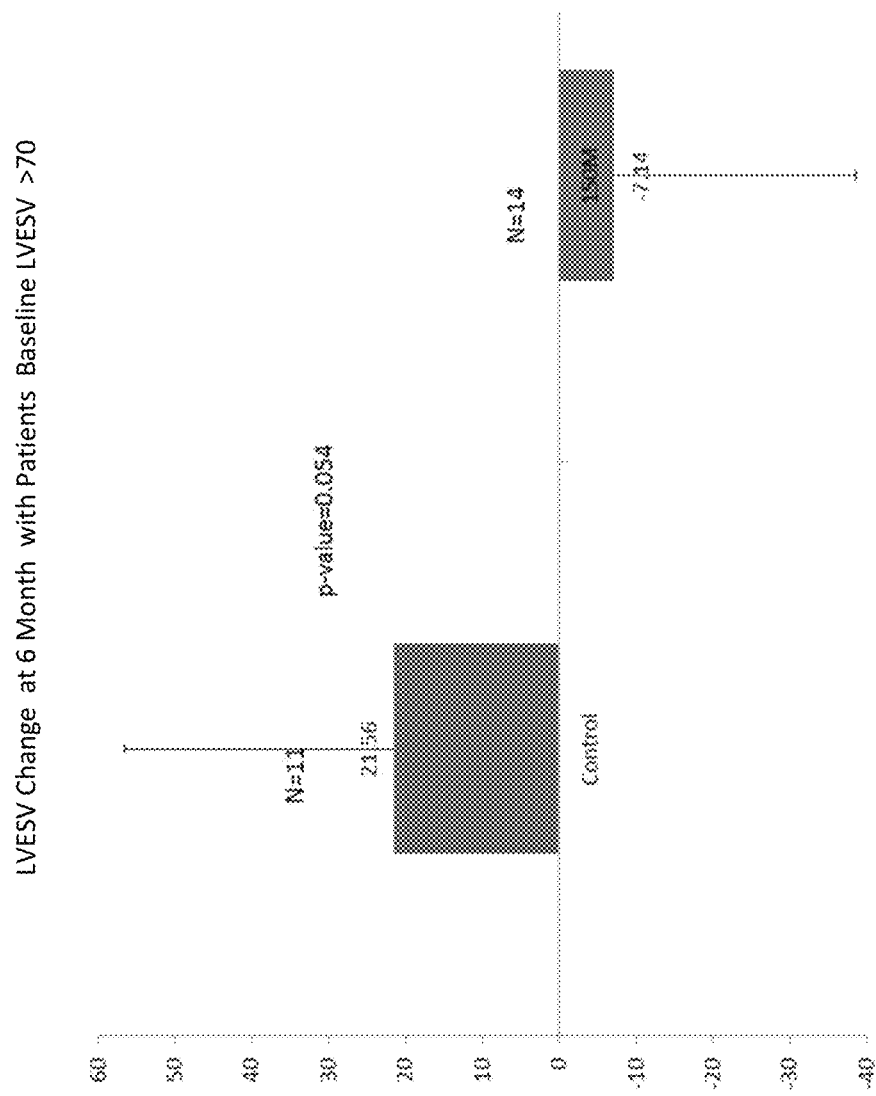
FIG. 4: shows the change in LVESV value at 6 months in placebo (control) and MPC administered subjects (150 million cells) striated according to a LVESV of greater than 70 mL.
Figure 5:
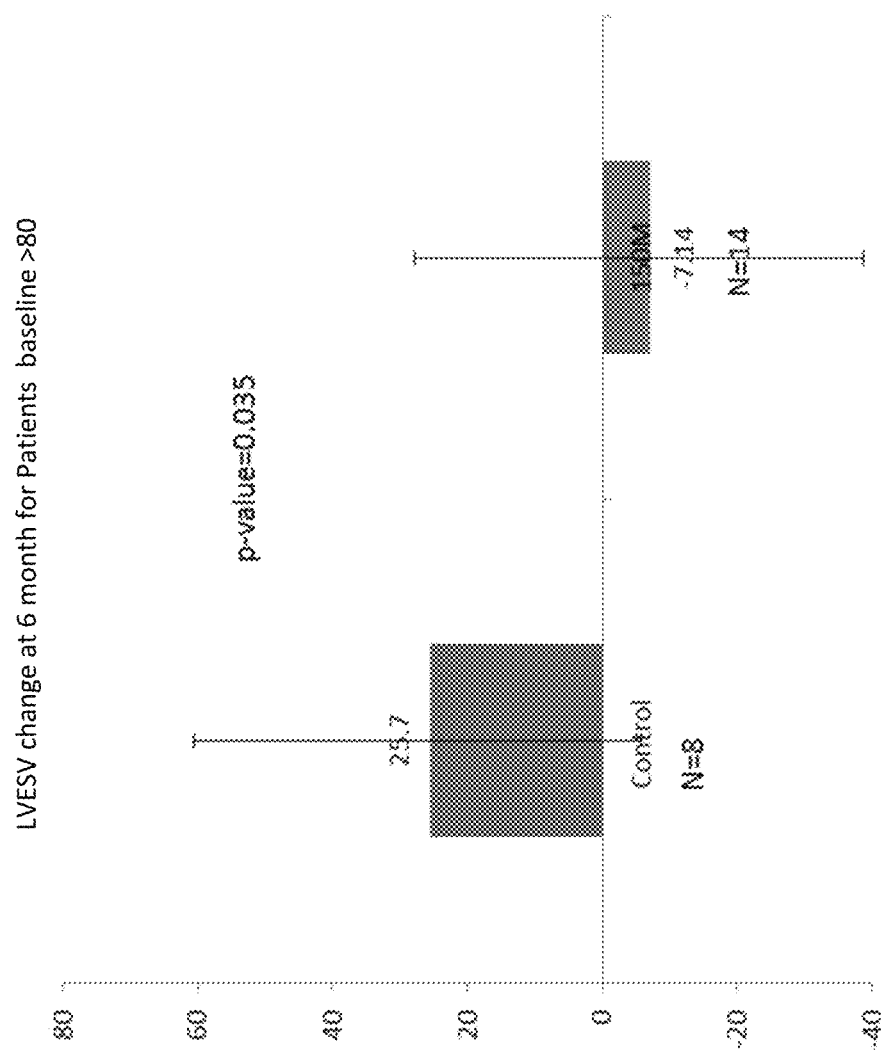
FIG. 5: shows the change in LVESV value at 6 months in placebo (control) and MPC administered subjects (150 million cells) striated according to a LVESV of greater than 80 mL.
Figure 6:
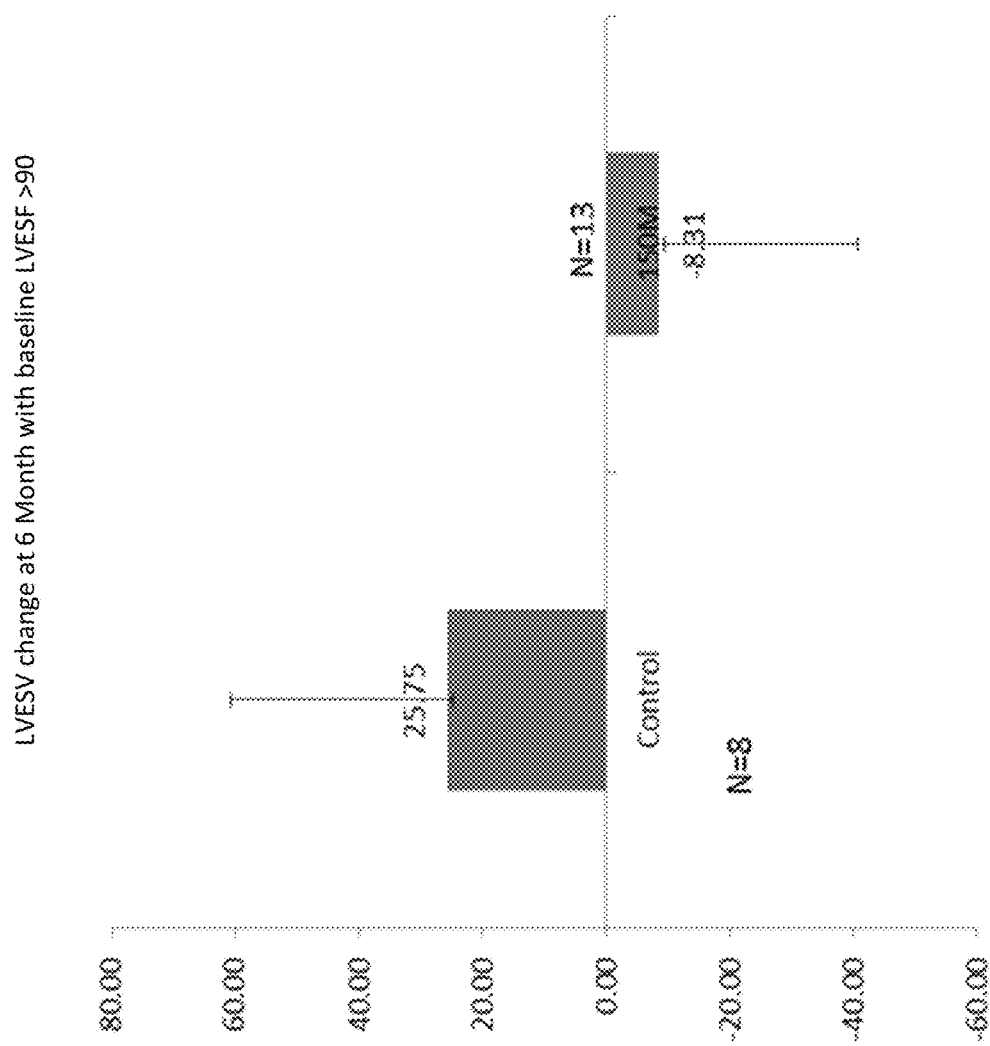
FIG. 6: shows the change in LVESV value at 6 months in placebo (control) and MPC administered subjects (150 million cells) striated according to a LVESV of greater than 90 mL.
Figure 7:
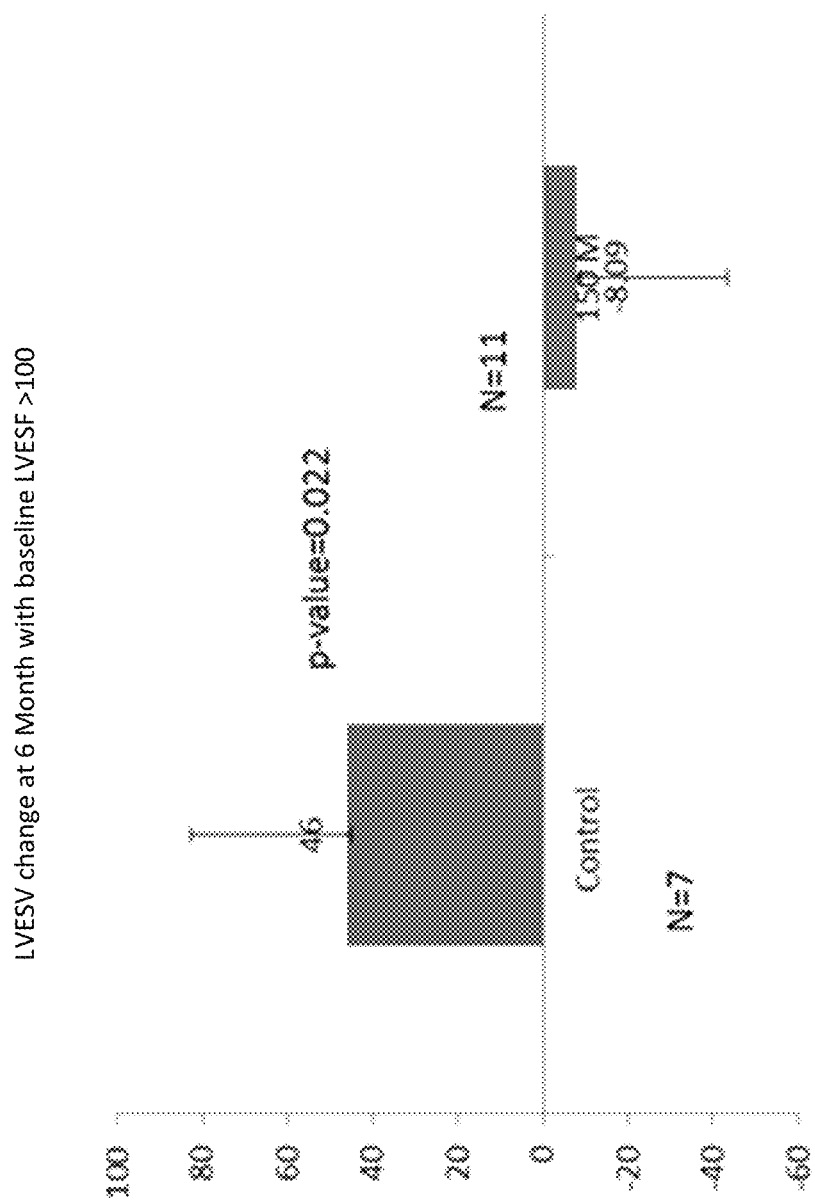
FIG. 7: shows the change in LVESV value at 6 months in placebo (control) and MPC administered subjects (150 million cells) striated according to a LVESV of greater than 100 mL.
Figure 8:
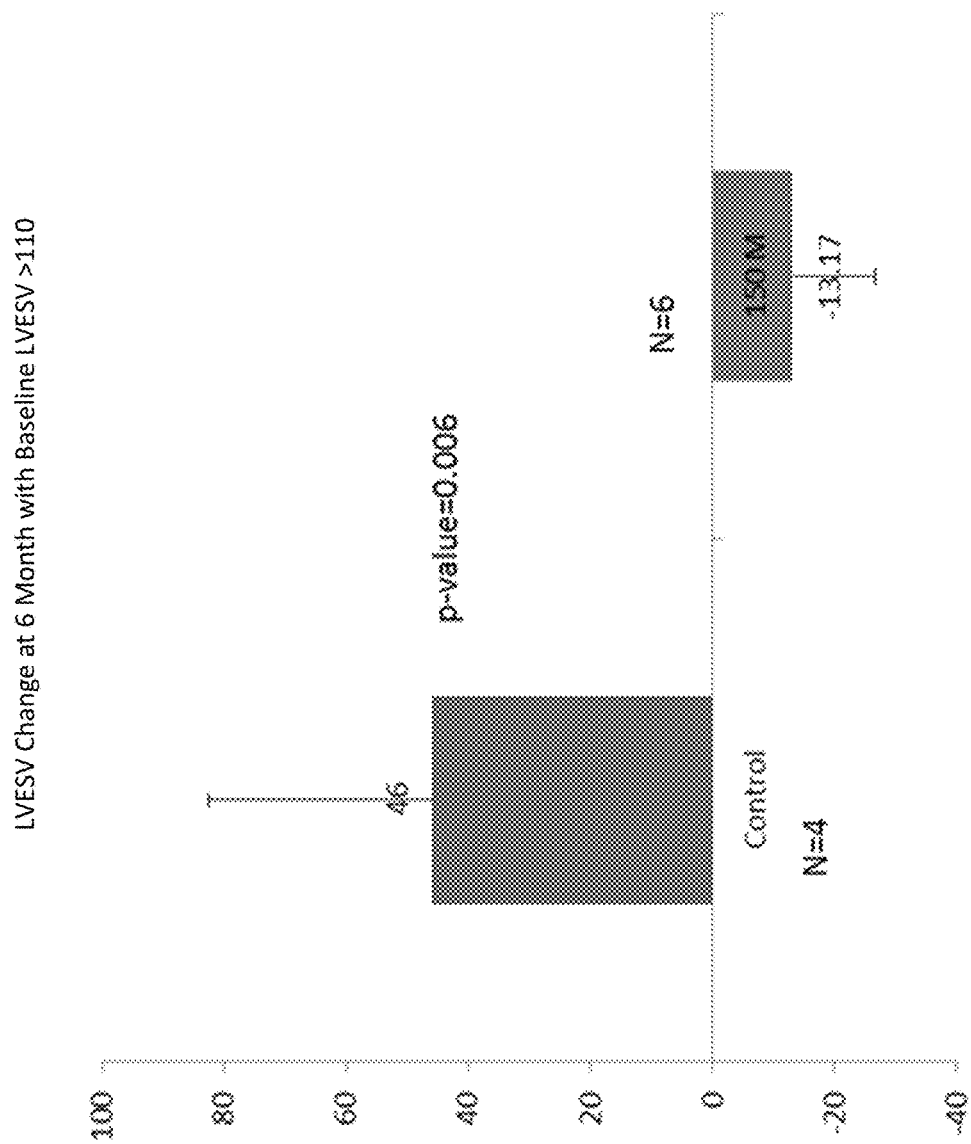
FIG. 8: shows the change in LVESV value at 6 months in placebo (control) and MPC administered subjects (150 million cells) striated according to a LVESV of greater than 110 mL.
Figure 9:
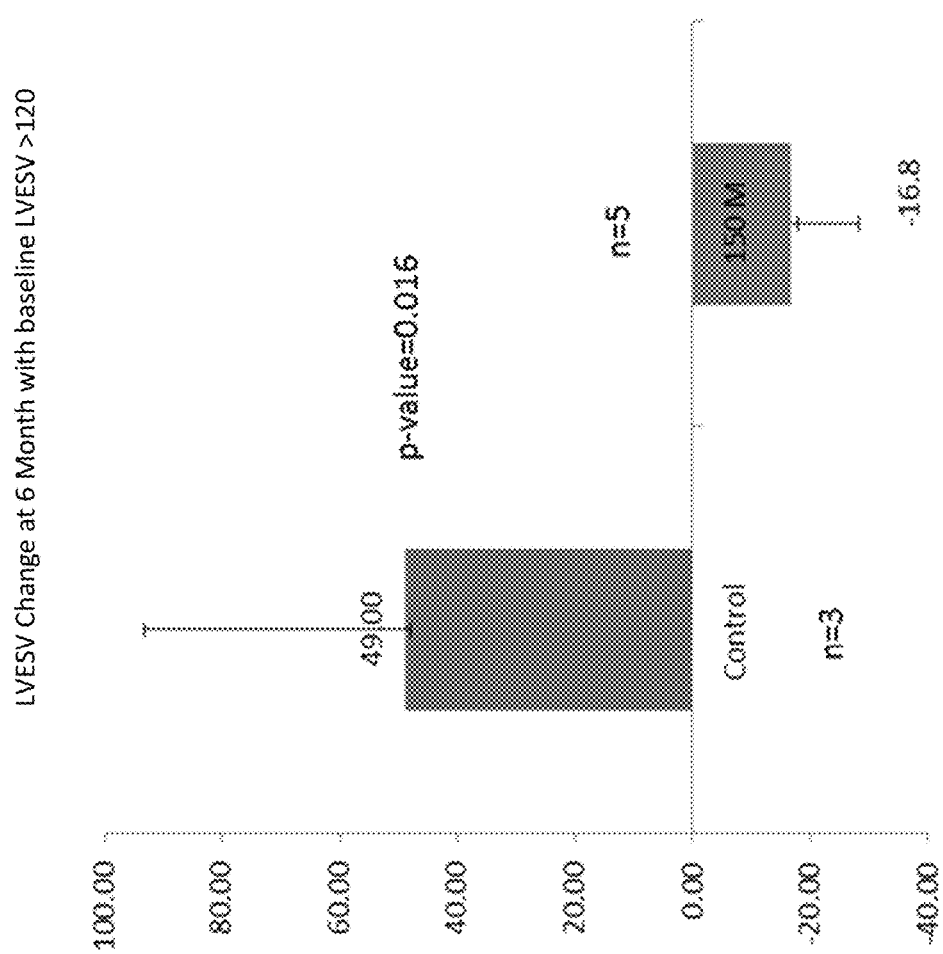
FIG. 9: shows the change in LVESV value at 6 months in placebo (control) and MPC administered subjects (150 million cells) striated according to a LVESV of greater than 120 mL.

There was an important trend towards statistical significance (p=0.095) for the difference between the percent of remestemcel-L vs. PLACEBO patients who were treatment responders at 6 months post the index AMI. Specifically, 60% of the remestemcel-L treated patients were treatment responders compared to 27% of placebo patients. This represented a 2.2 fold increase in the responder rate for the remestemcel-L group compared with the placebo group (FIG. 3).

Cohort Analysis for the Sub-Groups of "Responder" Vs "Non-Responder"

Although the responder rate for decrease in LVESV was 2.2 fold higher in the remestemcel-L group than in the placebo group, the mean changes at 6 months for parameters of LV remodeling and overall LV systolic function were similar for remestemcel-L and placebo responders (decreased LVESV, no change in LVEDV, and increased LVEF) compared with remestemcel-L and placebo non-responders (nominal increase in LVESV, large increase in LVEDV, and minimal increase in LVEF).

In contrast, the remestemcel-L treatment responder subjects demonstrated a larger decrease in LV infarct volume from baseline to month 6 (−18.8 g) than was noted for any other sub-groups (remestemcel-L non-responders=−7.1 g, PLACEBO responders=−4.8 g, and placebo non-responders=−9.1 g). The mean change in LV infarct volume for the 17 patients included in the latter three groups was −7.6 g. This differentiation in LV infarct volume for the remestemcel-L treatment responders is in marked contrast to the data generated for the LVESV, LVEDV, and LVEF analyses where the treatment responder data were generally similar for the remestemcel-L and placebo subjects.

Assuming a mean left ventricular mass of 130 g in patients with large infarcts after a proximal LAD occlusion (Stone et al. (2012) JAMA., 307:17, 1817-26), this represents a change in infarct size from approximately 30% at baseline to approximately 17% at 6 months in the remestemcel-L responders. This reduction in infarct volume is likely to have a major impact on the HF-MACE event rate over two years in this group (Wu et al. (2007) Stem Cells, 25:26, 48-59).

Thus, the remestemcel-L responders demonstrated:
  1) A 2.2 fold higher rate of achievement of the primary efficacy endpoint relating to LVESV (p=0.095);

2) A greater level of concordance between improvement in LV remodelling, improvement in overall LV systolic function and reduction in LV infarct volume.
3) A unique mechanism by which LVESV and adverse LV remodelling has been improved, namely by reduction in infarct volume.

Summary of Change in LV Remodeling, Overall
LV Function and LV Infarct Size (6 month-Baseline)
by Responder vs Non-responder Analysis

| TREAT-MENT | LVESV RESPONSE | ΔLVESV | ΔLVEDV | ΔLVEF | ΔLV INFARCT VOLUME |
|---|---|---|---|---|---|
| remestemcel-L | Responder | −22.7 mL | +3.1 mL | +16.9% | −18.8 g |
|  | Non-responder | +4.1 mL | +24.1 mL | +5.9% | −7.1 g |
| PLACEBO | Responder | −22.7 mL | −3.2 mL | +13.8% | −4.8 g |
|  | Non-responder | +11.3 mL | +23.9 mL | +2.6% | −9.1 g |

For the overall remestemcel-L group (n=10) vs. the placebo group (n=15) there were no significant differences for baseline demographics, time from onset of ischemic MI symptoms to the time of PCI, or incidence of TIMI perfusion flow grade 3 post PCI. There was a trend towards shorter time from PCI to infusion of investigational product and time from first ischemic MI symptoms to infusion of investigational product for the remestemcel-L group compared with the placebo group.

In conclusion, the intravenous administration of remestemcel-L 2-7 days post AMI helped to decrease LV infarct size, attenuate adverse LV remodelling, and improve overall LV systolic function at 6 months post the index event. It appears that the beneficial effects of remestemcel-L compared to placebo were evident in both the infarct region (decrease in infarct volume) and the remote myocardial areas (decrease in LVESV leading to increase in LVEF). It is anticipated that these findings would ultimately equate to a reduction in the incidence of development of heart failure in post-AMI patients at high risk for this condition.

Example 2

Correlation Between Disease Severity and Therapeutic Benefit of MPC on LVESV

FIGS. 4 through 9 show the change in LVESV in subjects evaluated at 6 months following administration of placebo (control) or MPCs ($1.5 \times 10^8$ mesenchymal precursor cells). The reduction in LVESV was correlated with the level of heart failure (as determined by measurement of baseline LVESV). Subjects were striated according to LVESV as shown below.

| LVESV cut-off value | Change in LVESV at 6 months | | |
|---|---|---|---|
|  | Placebo/control | MPC cell group | P value |
| >70 mL | 21.56 | −7.14 | 0.054 |
| >80 mL | 25.7 | −7.14 | 0.035 |
| >90 mL | 25.75 | −8.31 | 0.035 |
| >100 mL | 46 | −8.09 | 0.022 |
| >110 mL | 46 | −13.17 | 0.006 |
| >120 mL | 49 | −16.8 | 0.016 |

These data demonstrate that the greater the magnitude of baseline left ventricular contractile abnormality in subjects with chronic heart failure due to left ventricular systolic dysfunction, the more beneficial the MPC-related cardioprotective effect observed over a 6 month follow-up period. The data further demonstrates that the progressive adverse natural history associated with advance chronic heart failure can be beneficially altered by treatment with MPCs. Without wishing to be bound by theory, the findings are supportive of the paracrine cross-talk hypothesis in which tissue level biochemical/physiologic derangements create a local environment that facilitates MPC release of beneficial paracrine mediators. Thus the optimal benefit achieved by administration of MPCs in heart failure subjects, is seen in those subjects with the highest risk of disease progression, namely subjects with a baseline LVESV of >70 mL.

The invention claimed is:

1. A method for reducing the risk of heart failure-related major adverse cardiac events (HF-MACE) in a human subject characterized by the following:
    a) a left ventricular (LV) infarct;
    b) a proximal left anterior descending (LAD) arterial lesion;
    c) a left ventricular end systolic volume (LVESV) of greater than 70 ml;
    d) persistent left ventricular dysfunction; and
    e) a left ventricular ejection fraction (LVEF) of less than 40%,
which comprises administering to the subject a population of mesenchymal lineage precursor or stem cells and/or progeny thereof, or a combination of any of the foregoing in an amount effective to: (i) decrease the size of the subject's LV infarct; and (ii) improve the subject's LV systolic function so as to thereby reduce the subject's risk of HF-MACE for a period of at least six months after the administration.

2. The method of claim 1, wherein the effective amount of the population of mesenchymal lineage precursor or stem cells and/or progeny thereof is administered to the subject from about 1 to 7 days post-myocardial infarction.

3. The method of claim 1, wherein the subject has greater than 4× upper limit of normal creatine kinase-MB and/or troponin and/or myoglobin.

4. The method of claim 1, wherein the size of the subject's LV infarct is measured by cardiovascular magnetic resonance imaging (cMR).

5. The method of claim 1, wherein the population of mesenchymal lineage precursor or stem cells and/or progeny thereof is administered to the subject systemically.

6. The method of claim 1, wherein the population of mesenchymal lineage precursor or stem cells and/or progeny thereof is administered to the subject intravenously.

7. The method of claim 1, wherein the population of mesenchymal lineage precursor or stem cells and/or progeny thereof that is administered to the subject contains from $1.2 \times 10^8$ to $4 \times 10^8$ cells.

8. The method of claim 1, wherein the population of mesenchymal lineage precursor or stem cells and/or progeny thereof has been culture expanded prior to the administration.

9. The method of claim 8, wherein the population of mesenchymal lineage precursor or stem cells and/or progeny thereof has been culture expanded from a population of mesenchymal lineage precursor or stem cells enriched for STRO-1$^+$ cells.

10. The method of claim 8, wherein the population of mesenchymal lineage precursor or stem cells and/or progeny thereof has been culture expanded from a population of mesenchymal lineage precursor or stem cells enriched STRO-1$^{bright}$ cells.

11. The method of claim 1, wherein the population of mesenchymal lineage precursor or stem cells and/or progeny thereof is administered to the subject by intracardiac administration.

12. The method of claim 1, wherein the subject's LV infarct size is decreased by 10%.

13. The method of claim 1, wherein the subject's LV infarct size is decreased by 30%.

* * * * *